United States Patent
Takase et al.

(10) Patent No.: US 7,208,276 B2
(45) Date of Patent: Apr. 24, 2007

(54) PROBE CARRIER AND METHOD FOR ANALYZING THE PROBE CARRIER

(75) Inventors: Hiromitsu Takase, Tochigi (JP); Tadashi Okamoto, Kanagawa (JP); Toshiaki Aiba, Kanagawa (JP); Hiroyuki Hashimoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 481 days.

(21) Appl. No.: 10/728,707

(22) Filed: Dec. 4, 2003

(65) Prior Publication Data

US 2004/0152113 A1 Aug. 5, 2004

Related U.S. Application Data

(63) Continuation of application No. PCT/JP03/08092, filed on Jun. 26, 2003.

(30) Foreign Application Priority Data

Jun. 28, 2002 (JP) .............................. 2002-191533

(51) Int. Cl.
*C12Q 1/68* (2006.01)
(52) U.S. Cl. ..................... 435/6; 435/287.1; 435/287.2
(58) Field of Classification Search ..................... None
See application file for complete search history.

(56) References Cited

U.S. PATENT DOCUMENTS 5,601,980 A 2/1997 Gordon et al.
5,821,060 A 10/1998 Arlinghaus et al.
5,962,244 A * 10/1999 Lynch et al. .................. 435/15
6,528,264 B1 * 3/2003 Pal et al. ........................ 435/6

FOREIGN PATENT DOCUMENTS

| JP | 8210998 | 8/1996 |
| JP | 2000516727 | 6/1998 |
| JP | 11-187900 | 7/1999 |
| WO | 98/59362 | 12/1998 |

OTHER PUBLICATIONS

Addison et al. Antiviral Research vol. 48:27-37. 2000.*
Schena et al; "Quantitative Monitoring of Genb Expression Patterns with a Complementary DNA Microarray", Science, vol. 270, Oct. 20, 1995; pp. 467-470.
Arlinghaus et al, "Analysis of Biosensor Chips for Identification of Nucleic Acids", Anal. Chem, vol. 69, No. 18, Sep. 15, 1997, pp. 3747-3753.
John et al, "Time-of-Flight Secondary Ion Mass Spectrometry Analysis of Biological Materials", Secondary Ion Mass Spectrometry SIMS VIII, Proceedings of the 8th International Conference Amsterdam the Netherlands, Sep. 15-20, 1991, pp. 657-660; John Wiley & Sons.
Lazzeri, et al, Use of spin-coatd TXRF reference samples for ToF-SIMS metal contaminant quantification on silicon wafers; Surface and Interface Analysis 29, 200009, pp. 798-803.
Search Report—PCT/JP03/08092, Jun. 26, 2003.

* cited by examiner

*Primary Examiner*—Teresa E. Strzelecka
*Assistant Examiner*—Heather G. Calamita
(74) *Attorney, Agent, or Firm*—Morgan & Finnegan, LLP

(57) ABSTRACT

Nucleic acid probes arranged on a nucleic acid chip substrate in a matrix form can be analyzed quantitatively by TOF-SIMS with accuracy by forming a phosphorus-containing area which can be used as a standard on the substrate.

16 Claims, 11 Drawing Sheets

PROBE CARRIER AND METHOD FOR ANALYZING THE PROBE CARRIER

This application is a continuation of International Application No. PCT/JP03/08092, filed Jun. 26, 2003, which claims the benefit of Japanese Patent Application No. 2002-191533, filed Jun. 28, 2002.

BACKGROUND OF THE INVENTION

1. Field of the Invention

The present invention relates to a probe carrier such as what is called "nucleic acid chip" having a plurality of nucleic acid probe immobilized areas arranged on a carrier such as a substrate in a matrix form. The present invention also relates to a method for analyzing an amount of nucleic acid probes in each dot-like immobilized area formed on a probe carrier by time-of-flight secondary ion mass spectrometry (hereinafter abbreviated as TOF-SIMS).

2. Description of Related Art

A nucleic acid chip such as a DNA chip or RNA chip is now being used to acquire genetic information as in the analysis of a genome or the analysis of gene expression. The results of analysis using those chips are expected to provide important indices for diagnoses of cancer, hereditary diseases, lifestyle-related diseases, infectious diseases, and the like, and prognosis, determination of therapeutic strategy, and the like.

There are known several methods of producing the above nucleic acid chips. Taking a DNA chip as an example, typical DNA chip producing methods include one in which photolithography is used to synthesize DNA probes on a substrate sequentially (U.S. Pat. No. 5,405,783) and one in which pre-synthesized DNA or complementary DNA (cDNA) is supplied and bonded to a substrate (U.S. Pat. No. 5,601,980), JP H11-187900 A, "Science" Vol. 270, 467, 1995, etc.).

In general, the nucleic acid chip is produced by one of the above methods. When the nucleic acid chip is to be used for the above purposes, it is very important to know the amount of probes existent on each matrix, that is, density in order to ensure reliable analysis, i.e., determination and reproducibility. It is also important to know (imaging) what matrix form (shape, size and state) the probes are actually existent in. However, since the probes on the chip are existent in the form of a monomolecular film theoretically, a highly sensitive surface-analysis technique is required for the analysis of the probes.

As the highly sensitive surface-analysis technique, a method for labeling a probe with an isotope is known. However, since this method is complicated and dangerous and requires a special device and facility, it is not generally used in many cases.

Alternative methods include a method for labeling probes by fluorescence and a method for bonding a substance labeled with fluorescence to probes, that is, fluorescence hybridization. However, these methods involve problems with stability of a fluorochrome, quenching, non-specific adsorption of fluorochrome to the surface of a substrate and the determination (stability, reproducibility) of specific bonding (hybridization). Consequently, there are still remaining problems to be solved for the determination of the amount of probes themselves in many cases.

Alternatively, general highly sensitive surface-analysis methods include ATR making use of FT-IR (Fourier transform infrared spectroscopy) and XPS (X-ray photoelectron spectroscopy). However, it cannot be said that those methods attain sufficient sensitivity for the quantitative analysis of the probes of the nucleic acid chip or imaging. In particular, when general glass is used in the substrate of the nucleic acid chip, FT-IR (ATR) has a problem such as the influence of absorption by glass and XPS has a problem such as the influence of a charge-up, for example. Therefore, they may not be effective analysis methods in some cases.

Other highly sensitive surface-analysis methods include a DNA detection method making use of laser resonance ionization spectroscopy (RIS) as disclosed in U.S. Pat. No. 5,821,060. In this method, a laser beam having a wavelength corresponding to the ionization energy of an element of interest released from the surface of a sample is applied to ionize the element and detect this ionized element. As a method for releasing the element from the surface of the sample, a method using a laser beam is disclosed. However, this method has such problems that a large-size apparatus is required and that the element to be detected is limited.

As still another highly sensitive surface-analysis method is dynamic secondary ion mass spectrometry (dynamic-SIMS) which is not suitable for the analysis of an organic material such as a nucleic acid-related substance because an organic compound is decomposed into small fragment ions or particles during the generation of secondary ions and thereby chemical structure information obtained from its mass spectrum is poor.

On the other hand, there is known time-of-flight secondary ion mass spectrometry (TOF-SIMS) as highly sensitive surface-analysis method. TOF-SIMS is an analysis method for investigating what type of atom or molecule is existent on the outermost surface of a solid sample and has the following features.

That is, it can detect a trace component even when its amount is as small as $10^9$ atoms/cm$^2$ (corresponding to $1/10^5$ of a one-atomic layer on the outermost surface), can be used for both organic and inorganic materials, can measure all the elements and compounds existent on the surface and can effect imaging of secondary ions from a substance existent on the surface of the sample.

The principle of this method will be briefly described hereinbelow. When a pulse ion (primary ion) beam with high energy is applied to the surface of the solid sample under high vacuum, a constituent of the surface is released into vacuum by a sputtering phenomenon. Positively or negatively charged ions (secondary ions) generated at this point are converged in one direction by an electric field and detected at a fixed distance. When primary ions are applied to the surface of the solid sample in a pulse form, secondary ions which differ in mass are generated according to a composition of the surface of the sample. Since light ions fly faster than heavy ions, the mass of each of the generated secondary ions can be analyzed by measuring the time (time of flight) from the generation of the secondary ions to the detection of the ions. When the primary ions are applied, only secondary ions generated from the outermost side of the surface of the solid sample are released into vacuum, thereby making it possible to obtain information on the outermost surface (depth of about several Å to several nm) of the sample. Since the amount of the primary ions applied is extremely small in TOF-SIMS, the organic compound is ionized while it keeps its chemical structure, so that the structure of the organic compound can be known from its mass spectrum. For an insulating sample, a pulsed electron beam of low energy is applied to the positively charged surface of the sample when the pulsed primary ions are not irradiated in order to neutralize the positive charges accumulated on the surface of the solid sample, thereby making it possible to analyze the insulating sample. In addition, TOF-SIMS gives an ion image (mapping) of the surface of the sample to be measured by scanning a primary ion beam.

An example in which the nucleic acid in the form of a monomolecular film immobilized on the substrate is detected by TOF-SIMS has been already reported (Proceeding of the 12$^{th}$ International Conference on Secondary Ion Mass Spectrometry 951, 1999). In this example, the decomposed fragment ions of a base and the decomposed fragment ions of a phosphate backbone are enumerated as nucleic acid fragment ions detectable by TOF-SIMS.

As attempts to carry out quantitative analysis using TOF-SIMS, there are known one in which standard solutions having different concentrations are each applied to a clean silicon substrate, dried and measured by TOF-SIMS to obtain an analytical curve from a peak intensity of secondary ions from the resulting standard samples and compare it with the peak intensity of secondary ions from a sample to be analyzed (C. M. John et al., SIMS VIII, p. 657, Wiley and Sons, 1992) and one in which a standard sample for total reflection fluorescence X-ray analysis prepared by spin-coating a silicon substrate with a trace amount of a metal element to is used (P. Lazzeri et al., Surface and Interface Analysis, Vol. 29, 798 (2000)).

However, quantitative analysis by TOF-SIMS involves the following problems. That is, in the method reported by C. M. John et al. in which standard solutions having different concentrations are each applied to a clean silicon substrate, dried and measured by TOF-SIMS to obtain an analytical curve from the peak intensity of secondary ions from the resulting standard samples and compare it with the peak intensity of secondary ions from a sample to be analyzed, hydrocarbon and the like (contamination) are deposited on the prepared standard sample formed on the silicon substrate with time or the standard substance itself undergoes a chemical change, thereby losing reliability when the same standard sample is continuously used. For the above reasons, the standard solution must be prepared each time to improve determination accuracy, thereby making an operation troublesome.

The method reported by P. Lazzeri et al. in which a standard sample for total reflection fluorescence X-ray analysis prepared by spin-coating a silicon substrate with a trace amount of a metal element is used lacks reliability because the above surface contamination and oxidation occur when the standard sample is kept for a long time, and is not always suitable for measurement by TOF-SIMS in which a size of the area to be analyzed is several tens of μm to several hundreds of μm due to nonuniform distribution of the elements of interest when spin-coating is used. Further, the standard sample for total reflection fluorescence X-ray analysis has conductivity, whereas a nucleic acid chip may be formed on an insulating material substrate. In this case, TOF-SIMS measurement conditions which are determined by the standard sample on a silicon substrate may not always be measurement conditions for a nucleic acid chip, thereby causing an error due to differences in measurement conditions.

SUMMARY OF THE INVENTION

It is an object of the present invention to provide a method for analyzing nucleic acid probes arranged on a nucleic acid chip substrate in a matrix form by TOF-SIMS accurately, which solves the problems involved analysis by TOF-SIMS.

According to the present invention, there is provided a probe carrier including a probe immobilized area where a nucleic acid probe is immobilized on a carrier, wherein the carrier has a phosphorus-containing area that contains phosphorus in a predetermined concentration, and the phosphorus contained in the phosphorus-containing area is used as a standard for quantitative analysis of the nucleic acid probe by detecting the phosphorus of the nucleic acid probe.

According to the present invention, there is provided a method for analyzing a probe carrier having a probe immobilized area in which a nucleic acid probe is immobilized and a phosphorus-containing area that contains phosphorus in a predetermined concentration on a carrier, which comprises the steps of: detecting an amount of the phosphorus contained in the nucleic acid probe in the probe immobilized areas as a first signal intensity; detecting an amount of the phosphorus in the phosphorus-containing area as a second signal intensity; and quantitatively analyzing the nucleic acid probe in the probe immobilized area by standardizing the first signal intensity by using the predetermined concentration of the phosphorus in the phosphorus-containing area and the second signal intensity.

As the method for detecting the amount of phosphorus as the signal intensity, time-of-flight secondary ion mass spectrometry (TOF-SIMS) is preferable.

According to the present invention, an amount of nucleic acid probes on a probe carrier can be determined more accurately by forming a phosphorus-containing area which can be used as a standard for quantitative analysis of phosphorus that can be held stably on the nucleic acid probe carrier.

DESCRIPTION OF THE PREFERRED EMBODIMENTS

Figure 1A:
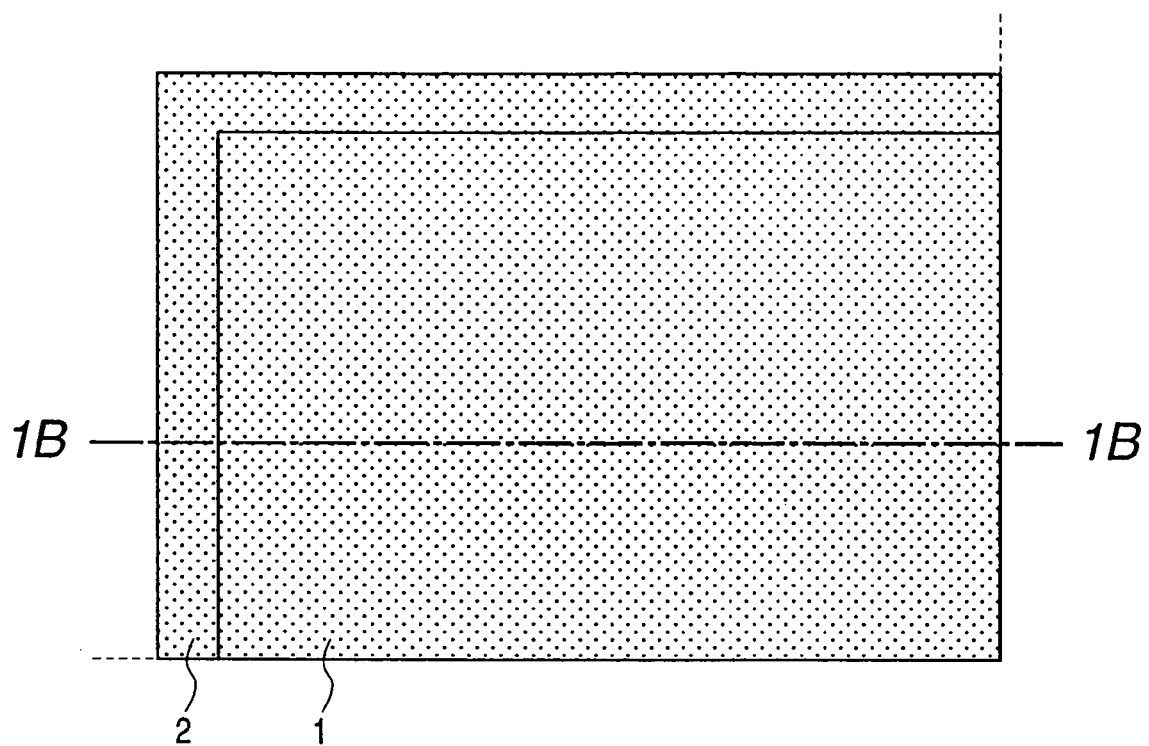
FIGS. 1A and 1B are schematic diagrams showing an example of a synthetic quartz substrate having a PSG film.

Probes immobilized on a carrier in the present invention can be bonded specifically to a specific targeted substance. For example, in the case of a nucleic acid such as DNA or RNA, when the probes have a complementary sequence to a base sequence of the targeted nucleic acid, hybrid bodies thereof can be formed.

The carrier can be selected from carriers having various shapes and formed of materials and is preferably a silicon substrate, metal substrate or resin substrate, for example. In addition, the carrier may be a suitably surface-treated silicon, metal or resin substrate.

The nucleic acid forming the probes is oligodeoxy nucleotide, polydeoxy nucleotide or nucleic acid analog typified by DNA such as complementary DNA (cDNA), RNA such as mRNA, tRNA or rRNA, or peptide nucleic acid (PNA) composed of peptide. At least one of them may be used. They may be immobilized on a carrier in a single-stranded state. The present invention can be applied to a hybrid body prepared by bonding a single-stranded nucleic acid immobilized on a carrier to another single-stranded nucleic acid by hybridization.

The nucleic acid probe can be immobilized on the carrier by a predetermined method. For example, a nucleic acid probe having a portion composed of a base sequence capable of hybridization with a targeted nucleic acid is bonded to a carrier by a linker as required. At this point, it is preferred to take into consideration the arrangement of bonded portions so that they do not affect hybridization.

In the present invention, a carrier having thereon a probe immobilized area in which nucleic acid probes are immobilized in a dot form, is called "probe carrier" and a carrier on which a plurality of or a large number of probe immobilized areas are each independently arranged at predetermined positions, is called "probe array".

A phosphorus-containing area used as a quantitative determination standard for the probe carrier of the present invention may be formed by implanting phosphorus into at least part of the carrier, formed as a film provided on at least part of the surface of the carrier, formed by incorporating phosphorus in the entire portion constituting the surface having the probe immobilized areas of the carrier, or formed by making the whole carrier of a phosphorus-containing material.

The concentration of phosphorus in the phosphorus-containing area is so set as to be a predetermined value and can be made constant in the depth direction of the carrier or can be allowed to have a distribution. For example, when a phosphorus-containing film is used or when phosphorus is contained in a material for forming the probe immobilized surface of the carrier or in the entire carrier, the concentration of phosphorus is preferably constant in the thickness direction. When the phosphorus-containing area is formed on at least part of the carrier by ion implantation, the integrated value of changes in the depth direction may be used as a known concentration of phosphorus.

The expression "constant in the depth direction of the carrier" means that the distribution of phosphorus concentration does not change in the depth direction or even when it changes slightly, it changes to such an extent that it can be used as a determination standard without any problem.

Further, a material which forms the nucleic acid probe immobilized surface of the carrier and contains phosphorus uniformly may also be used. The term "uniformly" in this case means that the distribution of phosphorus concentration in the whole material does not change or even when it changes slightly, it changes to such an extent that it can be used as a determination standard without any problem.

Preferred embodiments of the phosphorus-containing area of the carrier will be described hereinbelow.

(1) A Case Where the Phosphorus-Containing Area is Formed of a Film Containing Phosphorus:

In order to form a film-like phosphorus-containing area, it is preferred to use phosphorus silicate glass (PSG) or boron phosphorus silicate glass (BPSG) film.

To produce the PSG or BPSG film, chemical vapor deposition (CVD) is generally used. The chemical reaction formula is given below.

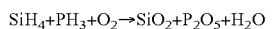

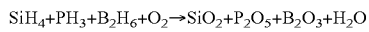

These films are formed on at least part of the surface of the substrate of what is called "nucleic acid chip" having a plurality of nucleic acid probes arranged on the substrate in a matrix form. The thickness of the film is not particularly limited, but generally set within a range of 2 nm to 10 µm. When the film is too thin, a phosphorus-containing film may be lost by sputter etching which will be described hereinafter. When the film is too thick, this increases the production cost of the substrate or causes the cracking of the film. Therefore, the thickness of the film is preferably set to be 10 nm to 200 nm.

The concentration of phosphorus in both the films is preferably set to be 0.001 to 30 wt %, particularly preferably 0.1 to 10 wt %. When the content of phosphorus is reduced and the film is made thick, cracking is liable to occur and attention should be paid.

To form the above phosphorus-containing film on part of the surface of the nucleic acid substrate, after the phosphorus-containing film is formed on the entire surface of the substrate, a technique such as mask etching may be used.

The surface of the above phosphorus-containing film is preferably made as flat as possible. This is to improve the measurement accuracy of TOF-SIMS which will be described hereinafter and the yield of a nucleic acid chip when the film is formed on the entire surface. Although the method for producing a PSG film having a flat surface is already disclosed in Japanese Patent No. 2983476, the present invention is not limited thereto.

For the distribution of phosphorus concentration in the depth direction of the phosphorus-containing area formed on the carrier, measurement values obtained by using a measurement sample produced under the same condition can be used. Methods which can be used for the standardization of this phosphorus concentration are given below. At least one of them may be used.

1) Secondary ion mass spectrometry: SIMS
2) Time-of-flight secondary ion mass spectrometry: TOF-SIMS
3) X-ray photoelectron spectroscopy: XPS
4) Auger electron spectroscopy: AES
5) Inductively coupled plasma atomic emission spectroscopy: ICP-AES
6) Inductively coupled plasma mass spectrometry: ICP-MS
7) Fourier transforms infrared spectroscopy: FT-IR Among those, the analyzing methods 1) to 4) are mainly used to confirm that the phosphorus concentration of a film which contains phosphorus and has a constant phosphorus concentration in the depth direction is actually constant in the depth direction. Among those, the methods 1) and 2) are preferably used. The method 2) is convenient because when it is used, after the analysis of a nucleic acid chip by TOF-SIMS described below, the same apparatus may be used to analyze the concentration of phosphorus in the depth direction. In this case, the film which contains phosphorus and has a constant phosphorus concentration in the depth direction does not need to be a different film produced under the same conditions and may be the same film. It is possible to obtain the absolute value of phosphorus concentration in the film which contains phosphorus and has a constant phosphorus concentration in the depth direction by using a sensitivity coefficient of phosphorus in the methods 1) to 4). However, for this purpose, these methods generally have lower determination accuracy than the following chemical analysis methods.

Out of the above methods, the analyzing methods 5) to 7) are used to obtain the total amount of phosphorus in the film which contains phosphorus and has a constant phosphorus concentration in the depth direction. With the methods 5) and 6), highly accurate determination results are obtained because the film is dissolved in a suitable acid before analysis. The concentration of phosphorus is obtained from this value, the density of the film and the thickness of the film. Although the concentration of phosphorus in the film can be measured easily by a transmission method when the film is formed on a silicon substrate in the method 7), it generally has lower determination accuracy than the methods 5) and 6). In the case of the method 7), it is preferred to measure the concentration of phosphorus in vacuum to eliminate the influence of moisture.

One of the features of the method of analyzing a probe carrier of the present invention is that the amount of a nucleic acid in each dot of the so-called nucleic acid chip having a plurality of dot-like nucleic acid probe immobilized areas arranged on a carrier in a matrix form is determined on the basis of the intensity of a signal detected in the dot area and the intensity of a signal detected in a film area which contains phosphorus and preferably has a constant phosphorus concentration in the depth direction. The above detected intensities of signals are each preferably the intensity of a secondary ion detected by flight-of-time secondary ion mass spectrometry (TOF-SIMS), particularly preferably the intensity of any one of $P^-$, $PO^-$, $PO_2^-$ and $PO_3^-$.

Another feature of the present invention is that the intensity of a signal detected in the film area which contains phosphorus and has a constant phosphorus concentration in the depth direction is the intensity of a signal obtained after the area is etched by sputtering in a predetermined amount. The concentration of phosphorus in the plane direction of the phosphorus-containing area such as a phosphorus-containing film is constant in a specific area used for quantitative analysis, for example, a primary ion application spot.

As will be described hereinafter, the nucleic acid probes are preferably immobilized on the substrate by covalent bonding. In this case, for example, in the process of surface treatment of the carrier, the surface of the carrier is covered with (N-β-(aminoethyl)-γ-aminopropyltrimethoxysilane) as a silane coupling agent having an amino group bonded thereto and N-maleimidocaproyloxysuccinimido (EMCS) as a crosslinking agent. Since various contaminants may adhere in a trace amount to the surface of the carrier at a pretreatment stage before analysis, when TOF-SIMS is used as the analysis method, sputter etching is indispensable. Therefore, sputter etching must be carried out until a film having a known phosphorus concentration is exposed. The sputter etching conditions are preferably obtained in advance. It is known that the (surface) composition is changed by the selective sputtering of a specific element in sputter etching. However, it is confirmed by SIMS that a PSG film produced under fixed conditions has a constant phosphorus concentration in the depth direction. Therefore, conditions under which the phosphorus concentration of a PSG film having a known phosphorus concentration is not changed by the sputter etching of the surface layer are set.

When TOF-SIMS is used, the method of analyzing a probe carrier according to the present invention has such a feature that the image of secondary ions derived from the nucleic acid probes can be quantitatively displayed.

In the method of analyzing a probe carrier of the present invention, when the intensity of secondary ions released from each dot of the probe carrier and the intensity of secondary ions released from a film which is formed on at least part of the surface of the probe carrier, contains phosphorus and preferably has a constant phosphorus concentration in the depth direction are corrected with their secondary ionization efficiencies (sensitivity) or the like, quantitative evaluation is made possible. In this case, TOF-SIMS analytical conditions are made to be the same in these two areas.

Figure 6:
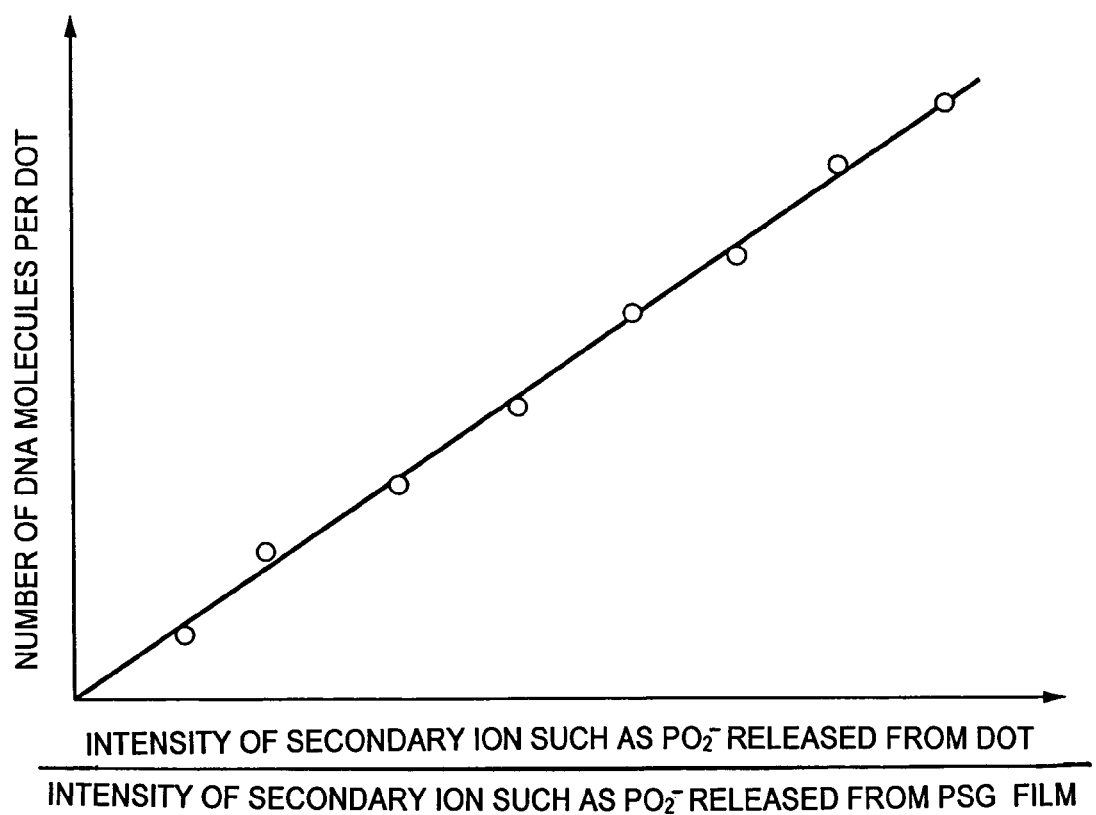
FIG. 6 is a graph showing an example of an analytical curve for obtaining the number of DNA molecules per dot by TOF-SIMS, which can be used as the analytical curve of a phosphorus-containing substrate by using an intensity from the substrate in place of the PSG film.

A standard probe immobilized area whose nucleic acid probe density has been obtained by chemical analysis or the like may be formed on a carrier having a film which contains phosphorus and preferably has a constant phosphorus concentration in the depth direction to obtain the relational expression (analytical curve) of the above two intensities. A specific example of the above relational expression (analytical curve) is shown in FIG. 6. By obtaining this relational expression (analytical curve), the number of DNA molecules per dot, that is, the density of nucleic acid probes can be evaluated based on the intensity of a secondary ion such as $P^-$, $PO^-$, $PO_2^-$ or $PO_3^-$ released from the above film which contains phosphorus and has a constant phosphorus concentration in the depth direction.

The above intensity of the secondary ion is not a counting rate but preferably integrated intensity counted for a certain time under certain conditions. More specifically, when the dose of the primary ions is set to a fixed value of $1\times10^{12}/cm^2$ or less which is called "static condition", the intensity of the secondary ion is preferably a count value of secondary ions released from a certain area, such as $P^-$, $PO^-$, $PO_2^-$ or $PO_3^-$. The dose of the primary ions must be set to $1\times10^{14}/cm^2$ or less. As the intensity of the secondary ions released from the above film which contains phosphorus and has a constant phosphorus concentration in the depth direction, such as $P^-$, $PO^-$, $PO_2^-$ or $PO_3^-$, the dose of the primary ions which is beyond the above static condition may be used (the dose of the primary ions must be the same each time).

(2) A Case Where a Phosphorus-Containing Area is Formed by Implanting Phosphorus Ions The phosphorus-containing area can be formed by using a material which allows for the implantation of phosphorus ions as the carrier and by setting arbitrary acceleration energy for the implantation of phosphorus ions and an arbitrary amount of phosphorus ions injected. As will be described hereinafter, when the measurement of a depth profile in the standard area is carried out by TOF-SIMS, a relatively long measurement time is needed because sputtering and measurement are carried out independently. Therefore, the acceleration energy for ion implantation is preferably set as low as possible to make the distribution depth of an injected element shallow. It is also preferred to perform the ion implantation of a large amount of an element.

Examples of the primary ion used for measurement by TOF-SIMS include $Cs^+$ ion and $Ga^+$ ion. Examples of the secondary ion species include $P^-$, $PO^-$, $PO_2^-$ and $PO_3^-$ derived from a phosphate unit in a nucleic acid when the nucleic acid probe is DNA, RNA, complementary DNA (cDNA) or complementary RNA (cRNA) as mentioned above. As for an electron beam which is used with an insulating material substrate such as a glass substrate for a nucleic acid chip, suitable application conditions must be determined in consideration of the pulse width and frequency of the primary ion and the dielectric constant of the sample.

$P^-$ is detected in the standard area into which phosphorus ions have been injected. Since the standard area which is formed on the substrate of a nucleic acid chip by ion implantation and each dot of the nucleic acid chip differ from each other in the main component, strictly, determination cannot be carried out simply by comparing the intensity of $P^-$, $PO^-$, $PO_2^-$ or $PO_3^-$ detected in the standard area with the intensity of $P^-$ detected in each dot of the nucleic acid chip (matrix effect). In consideration of this, sensitivity must be corrected in advance. In order to correct the sensitivity, a large number of nucleic acid dots formed separately under the same conditions as nucleic acid dots of interest are dissolved and analyzed chemically, a correction value for converting sensitivity coefficients is obtained from the sensitivity coefficient 1 of a nucleic acid dot obtained from the average formation density of the obtained nucleic acid dots and the average intensity of secondary ions in the nucleic acid dots of interest on the nucleic acid chip substrate and a sensitivity coefficient 2 obtained from the amount of implantation in the ion injected area and the intensity of the secondary ion in that area, then the formation density of each nucleic acid dot of interest on the substrate of the nucleic acid chip is determined based on the standard area (phosphorus ion injected area) of the substrate. Since a sensitivity coefficient is determined for each measurement in this method, a highly accurate formation density value can be determined even when the measurement date is different.

The feature of the method of analyzing a nucleic acid chip of the present invention is that the form of each nucleic acid dot is displayed together with the nucleic acid formation density distribution thereof.

(3) A Case Where a Phosphorus-Containing Area is Formed by Using a Phosphorus-Containing Carrier (Substrate)

The phosphorus-containing area referred to in the present invention can be formed on a probe carrier by using a material which contains phosphorus uniformly as the carrier. In this case, preferred examples of the carrier include a glass substrate, an Si-containing substrate and an Si-free substrate. The content (weight ratio) of phosphorus in the carrier is preferably 0.1 ppm to 10%. The phosphorus-containing area is used as a standard for determination and the secondary ion for carrying out determination by TOF-SIMS may be $P^-$, $PO^-$, $PO_2^-$ or $PO_3^-$ as in the above case. The intensity of a signal detected in the area including only the carrier (nucleic acid probe unimmobilized area) is preferably the intensity of a signal obtained after the area is etched by sputtering in a predetermined amount.

The substrate of the nucleic acid chip and the method of analyzing a biochip of the present invention will be described hereinbelow with reference to FIGS. 6, 10A to 10C, 11 and 12.

Figure 10A:
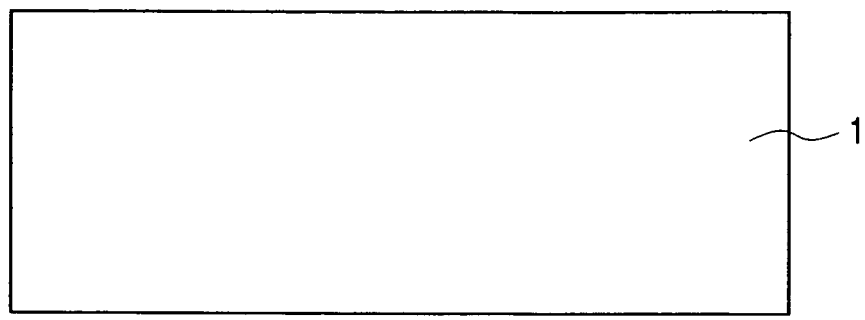
FIGS. 10A, 10B and 10C are schematic sectional views showing a method for producing the nucleic acid chip substrate of the present invention.
Figure 10B:
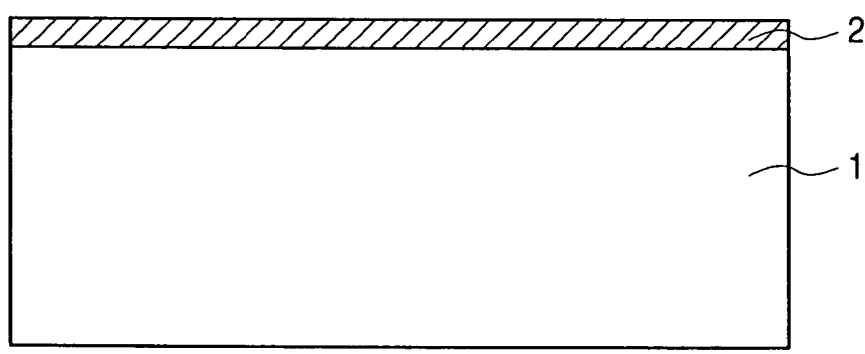
Figure 10C:
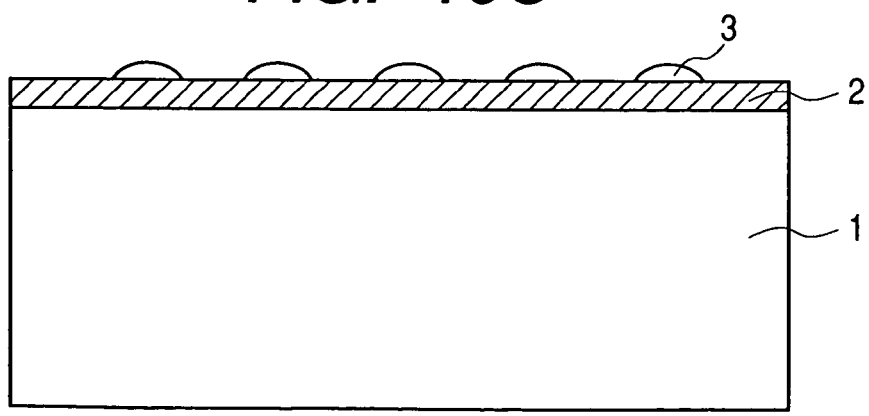
Figure 11:
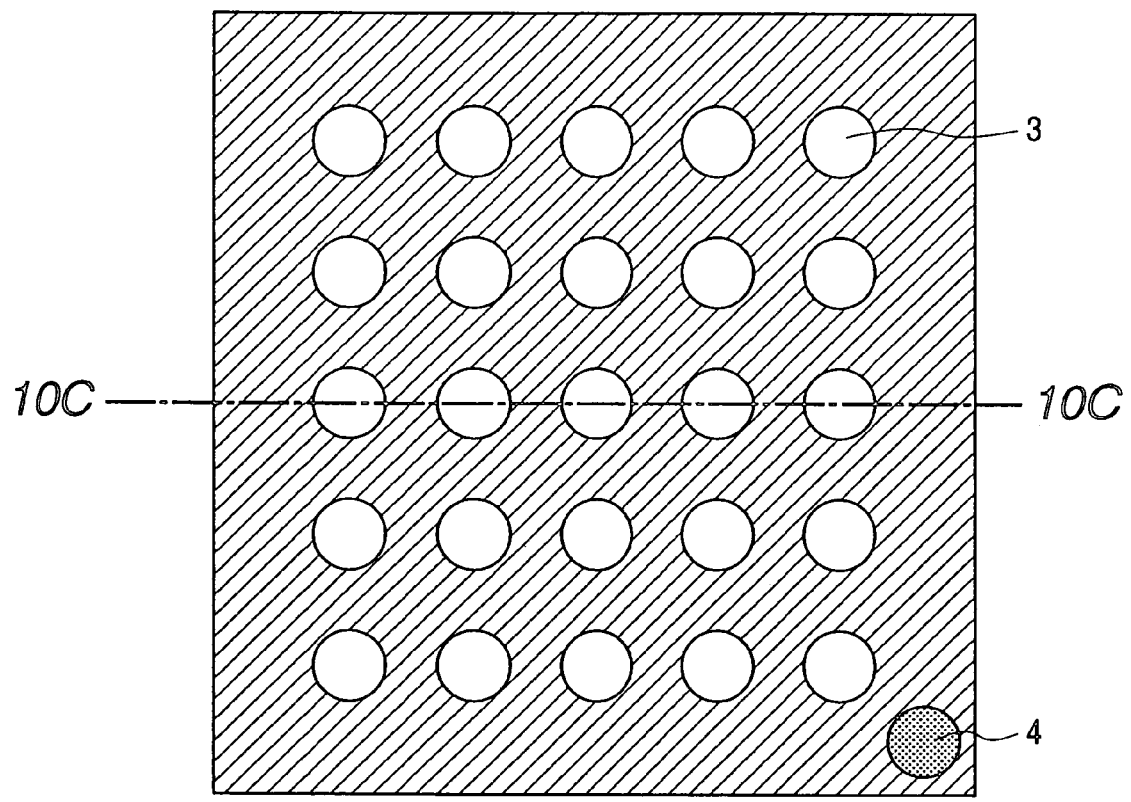
FIG. 11 is a schematic plan view of the nucleic acid chip substrate of the present invention.
Figure 12:
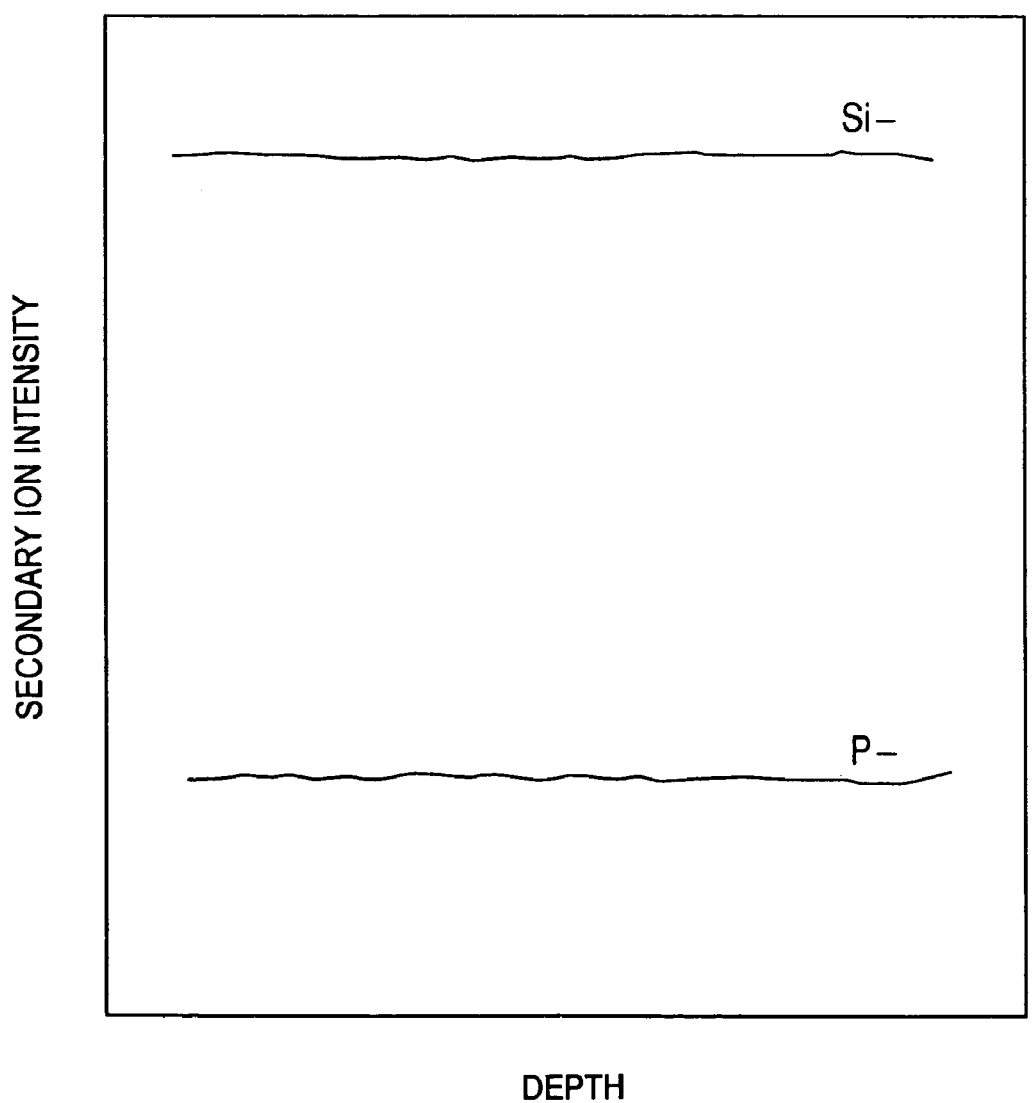
FIG. 12 is a schematic diagram showing an example of a depth profile of an intensity of a secondary ion released from a substrate containing phosphorus.

FIGS. 10A to 10C are diagrams showing the method of producing the substrate of the nucleic acid chip. FIG. 11 is a schematic plan view of the substrate of the nucleic acid chip having a probe array prepared by forming a plurality of nucleic acids on the substrate in a spot-like form. FIG. 10C is a schematic sectional view taken along the line 10C—10C of FIG. 11. In those figures, reference numeral 1 denotes a substrate; 2, a surface treated layer made from an organic material; 3, a nucleic acid dot; and 4, a standard area (which may be set anywhere in a probe-free area of the substrate) used as a standard for quantitative analysis. Further, FIG. 12 shows an example of the depth profile of the intensity of a secondary ion released from a substrate (that is, a standard area) containing phosphorus. FIG. 6 shows an example of an analytical curve for obtaining the number of DNA molecules per dot by TOF-SIMS.

The method of producing a probe array shown in FIGS. 10A, 10B and 10C and FIG. 11 will be described hereinbelow based on a known method (method disclosed in JP H11-187900 A).

(1) Preparation and Cleaning of Substrate

A substrate containing phosphorus to be used as a substrate for a nucleic acid chip was prepared and cleaned (FIG. 10A).

The substrate containing phosphorus may be one selected from the group consisting of a glass substrate, Si substrate, metal substrate and resin substrate, and is not particularly limited if it is not inconvenient for the bonding and analysis of a probe.

Among those, the glass substrate may be a silicate glass containing Si or a non-silicate glass containing no Si and is not particularly limited if it is not inconvenient for the bonding and analysis of a probe.

Further, the glass substrate among those substrates may be a crystallized glass substrate containing a crystal component or an amorphous glass substrate which does not contain a crystal component and is not particularly limited if it is inconvenient for the bonding and analysis of a probe.

The target nucleic acid chip of the present invention generally measures 1 cm×1 cm, 1 inch×1 inch (25.4 mm×25.4 mm) or is as large as a slide glass sheet (for example, 26 mm×76 mm) in outer shape and contains a matrix arranged (surface).

The content of phosphorus in the phosphorus-containing substrate is not particularly limited if it can be used as a standard sample for quantitative analysis in each analyzing method. When the analyzing method is TOF-SIMS, the content (weight ratio) of phosphorus is desirably 0.1 ppm to 10%.

Further, although the composition of the phosphorus-containing substrate used as a standard for quantitative analysis is desirably known, it may be actually obtained by various analysis methods or a value guaranteed by a manufacturer may be used if it is reliable. It is not particularly limited if it is not inconvenient for the bonding and analysis of a probe.

The composition of a substrate which contains phosphorus uniformly is desirably uniform at a bulk level.

Even when the composition of the bulk is uniform, the composition of the outermost surface of the substrate may be slightly different from the composition of the bulk. In this case, when a measurement value at a position deeper than the outermost surface of the substrate (position having the composition of the bulk) is used as a standard for quantitative analysis, the analyzing method of the present invention may be employed.

In order to clean the substrate, the substrate may be immersed in a cleaning solution or given ultrasonic vibration is applied to a cleaning solution. The cleaning method is not particularly limited if it is not inconvenient for the bonding and analysis of a probe.

Further, the cleaning solution for the substrate may be pure water, a solution prepared by diluting a cleaner, or a solution prepared by diluting an alkali, and is not particularly limited if it is not inconvenient for the bonding and analysis of a probe.

(2) Surface Treatment

The surface treatment of the substrate is then carried out to form a surface treated layer 2 formed from an organic material on the substrate 1 (FIG. 10B).

The surface treatment of the substrate is carried out to promote the immobilization of nucleic acid probes on the substrate which is preferably carried out by covalent bonding but is not particularly limited if it is not inconvenient for the bonding and analysis of a probe.

The surface treating agent for the substrate is a silane coupling agent or crosslinking agent and is not particularly limited if it is not inconvenient for the bonding and analysis of a probe.

(3) Preparation of Nucleic Acid

A nucleic acid used as the probes of a nucleic acid chip substrate is then prepared.

Examples of the nucleic acid include DNA, RNA and peptide nucleic acid (PNA).

(4) Formation of Probes on Substrate

A nucleic acid chip having the plural probes 3 containing a nucleic acid formed on the substrate 1 having the surface treated layer 2 made from the organic material is prepared (FIG. 10C). FIG. 10C is a schematic sectional view taken along the line 10C—10C of FIG. 11.

The method of forming probes may be one in which the nucleic acid is synthesized on the surface sequentially or one in which the nucleic acid is synthesized in advance and then supplied to the surface of the nucleic acid chip and is not particularly limited if it is not inconvenient for the bonding and analysis of a probe.

The method of supplying the previously synthesized nucleic acid to the surface of the nucleic acid chip may be an ink jet method and is not particularly limited if it is not inconvenient for the bonding and analysis of a probe.

The ink jet method as the method of supplying the nucleic acid to the surface of the nucleic acid chip may be a piezo jet method or thermal jet method and is not particularly limited if it is not inconvenient for the bonding and analysis of a probe.

(5) Analysis of Probes on Nucleic Acid Chip Substrate

The probes on the nucleic acid chip substrate are analyzed next.

In this analysis, the amount of the nucleic acid existent in each probe is determined based on the intensity of a signal detected in an area where the nucleic acid probes are existent and the intensity of a signal detected in an area of the substrate alone (standard area).

The signal used for the analysis of the probes may be the intensity of a secondary ion detected by time-of-flight secondary ion mass spectrometry (TOF-SIMS).

In TOF-SIMS measurement, the used TOF-SIMS apparatus may be of a sector type or reflectron type and is not particularly limited if it is not inconvenient for analysis.

In the TOF-SIMS measurement, the primary ion species may include $Cs^+$ ion or $Ga^+$ ion and is not particularly limited if it is not inconvenient for analysis.

Further, in the TOF-SIMS measurement, the secondary ion species may include $P^-$, $PO^-$, $PO_2^-$ or $PO_3^-$ derived from phosphate in a nucleic acid when the nucleic acid of the probes and the nucleic acid introduced by hybridization are DNA, RNA, complementary DNA (cDNA) or complementary RNA (cRNA).

The above intensity of the secondary ion is not a counting rate but preferably integral intensity counted for a certain time under certain conditions. Exactly speaking, when the dose of the primary ion is set to a fixed value of $1\times10^{12}/cm^2$ or less which is called "static condition", the intensity of the secondary ion is preferably a count value of secondary ions released from a certain area, such as $P^-$, $PO^-$, $PO_2^-$ or $PO_3^-$. The dose of the primary ion must be at least $1\times10^{14}/cm^2$. As the intensity of the secondary ion released from the above substrate which contains phosphorus, such as $P^-$, $PO^-$, $PO_2^-$ or $PO_3^-$, the dose of the primary ion which is beyond the above static condition may be used (the dose of the primary ion must be the same every time).

Further, when the conductivity of the substrate is poor in the TOF-SIMS measurement, the application of an electron beam or magnetic field may also be performed in combination to suppress charge-up.

A description is subsequently given of the quantitative analysis of the nucleic acid probes of a nucleic acid chip by TOF-SIMS.

In the method of analyzing a nucleic acid chip of the present invention, the intensity of the secondary ion released from each dot in the nucleic acid chip and the intensity of the secondary ion released from the substrate containing phosphorus are corrected with their secondary ionization efficiencies (sensitivities) or the like to allow quantitative evaluation. An example of the depth profile of the intensity of the secondary ion released from the substrate containing phosphorus is shown in FIG. 12.

A standard nucleic acid chip whose probe nucleic acid density has been obtained by chemical analysis or the like is formed on a substrate containing phosphorus to obtain the relational expression (analytical curve) between the above two intensities. An example of the above relational expression (analytical curve) is shown in FIG. 6. By obtaining the above relational expression (analytical curve), the number of DNA molecules per dot, that is, the probe nucleic acid density can be evaluated based on the intensity of the secondary ion released from the substrate containing phosphorus, such as $P^-$, $PO^-$, $PO_2^-$ or $PO_3^-$.

(6) Display of an Image of the Formation Density Distribution of Probes on Nucleic Acid Chip Substrate The primary ion is scanned over the surface of a sample by setting an area including a plurality of DNA probes in the same nucleic acid chip substrate to display the generated secondary ion at each scanning point. Similar measurement is made and the count value of $PO_3^-$ obtained at each scanning point is classified into different levels, and a quasi color is set for each level to obtain the intensity distribution of the secondary ion. That is, the formation density distributions can be quantitatively compared.

The method of analyzing a chip of the present invention can be applied when the nucleic acid contained in each dot of the nucleic acid chip includes only a probe nucleic acid and when the nucleic acid includes a probe nucleic acid and a targeted nucleic acid introduced by hybridization with the probe nucleic acid.

The method of the present invention is preferably applied when the nucleic acid contained in each dot of the nucleic acid chip includes a PNA probe nucleic acid and a DNA targeted nucleic acid introduced by hybridization with the probe nucleic acid and when the nucleic acid contained in each dot of the nucleic acid chip includes a DNA or RNA probe nucleic acid and a DNA targeted nucleic acid introduced by hybridization with the probe nucleic acid.

The method of analyzing a chip of the present invention can be applied when the nucleic acid contained in each dot of a probe carrier (probe immobilized area) includes only a nucleic acid probe and further when the nucleic acid includes a nucleic acid probe and a targeted nucleic acid introduced by hybridization with the nucleic acid probe.

The method is preferably applied when the nucleic acid contained in each dot of a probe carrier includes a PNA nucleic acid probe and a DNA targeted nucleic acid introduced by hybridization with the nucleic acid probe and further when the nucleic acid contained in each dot of a probe carrier includes a DNA or RNA nucleic acid probe and a DNA targeted nucleic acid introduced by hybridization with the nucleic acid probe.

The target probe carrier of the present invention generally measures 1 cm×1 cm, 1 inch×1 inch (25.4 mm×25.4 mm) or is as large as a slide glass sheet (for example, 26 mm×76 mm) in outer shape and contains a matrix arranged (surface). As mentioned above, the present invention relates to a method of analyzing the composition of the substrate of what is called "probe carrier" having a plurality of bio-related substances arranged on a substrate in a matrix form and the composition of each matrix on the surface of the substrate.

The probes are desirably bonded to the surface of the substrate by covalent bonding in consideration of stability.

A known process may be used for various processes for producing the probe carrier of the present invention. The probes may be synthesized on the surface of a carrier sequentially, or the probes may be synthesized in advance and then supplied to the surface of a carrier. When an ink jet method is used as a method of supplying the probes to the surface of the carrier, dot-like nucleic acid probe immobilized areas can be arranged on the carrier finely at a high density, as required, in a matrix form. The ink jet method may be a known piezo jet method or thermal jet method.

An example of a nucleic acid and a fragment ion specific to the nucleic acid is given below although not limited thereby. Since the nucleic acid has a backbone composed of a phosphoric acid diester, any one of $P^-$, $PO^-$, $PO_2^-$ and $PO_3^-$, which is the fragment ion of the backbone of the above phosphoric acid can be preferably detected as the fragment ion. As for the nucleic acid, in a case where the nucleic acid is DNA, there are listed adenine, thymine, guanine and cytosine as a base, whereas in a case where the nucleic acid is RNA, uracil is included in place of thymine as a base, so that there are five bases in total. Since PNA which is a typical nucleic acid analog has four bases which are adenine, thymine, guanine and cytosine, the fragment ions of these bases, that is, (adenine-H)$^-$, (thymine-H)$^-$, (guanine-H)$^-$, (cytosine-H)$^-$ and (uracil-H)$^-$ may be used as the secondary ion. The intensities of the fragment ions derived from these bases are proportional to the amount of the bases contained in each probe. Information on base sequence is generally not obtained by TOF-SIMS. Analytical values obtained from the fragment ions from these bases can be standardized by using the phosphorus-containing area as a standard.

Since the backbone of PNA is composed of peptide bonds, the fragment ion of the peptide bond can be advantageously used for TOF-SIMS detection.

EXAMPLES

Examples are given below to more specifically describe the present invention. The present invention is not limited by those examples.

Example 1

Manufacture of Synthetic Quartz Substrate Having a PSG Film

Figure 1B:
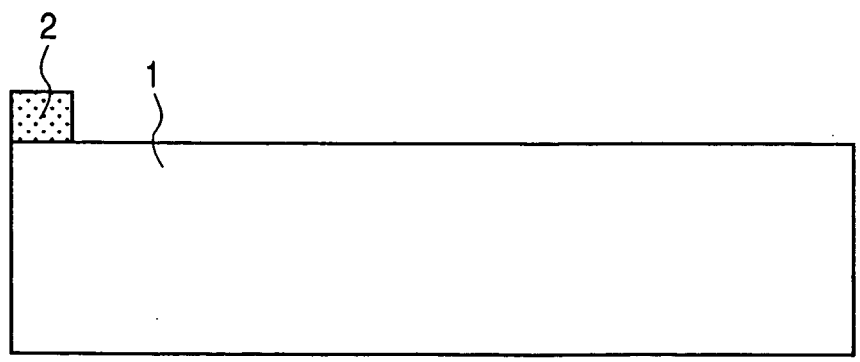

FIGS. 1A and 1B show the manufactured synthetic quartz substrate having a PSG film. FIG. 1A is a plan view and FIG. 1B is a sectional view taken along the line 1B—1B of FIG. 1A. Reference numeral 1 denotes the synthetic quartz substrate and reference numeral 2 denotes the PSG film. The method of manufacturing the substrate will be described below with reference to those figures.

The synthetic quartz substrate measuring 25.4 mm×25.4 mm×1 mm was placed in a rack and immersed in a cleaner for ultrasonic cleaning (Branson: GPIII) which was diluted with pure water to 10% for one night. Thereafter, ultrasonic cleaning was carried out in the cleaner for 20 minutes and then the cleaner was washed off with water. After rinsing in pure water, ultrasonic treatment was further carried out in a container filled with pure water for 20 minutes. The substrate was then immersed in a 1N sodium hydroxide aqueous solution previously heated at 80° C. for 10 minutes. Subsequently, the substrate was washed with water and pure water and then dried by blowing nitrogen gas.

This substrate was then introduced into a (B)PSG film forming device and a PSG film was formed on the entire surface of the substrate by using $SiH_4$, $PH_3$ and $O_2$ raw material gases. The temperature of the substrate was 400° C., the concentration of phosphorus was 3.0 wt %, and the thickness of the film was 1 μm. The concentration of phosphorus was determined as follows. PSG films were each formed on a silicon substrate under various conditions by changing the temperature of the substrate and the mixing ratio of raw material gases. The PSG films were analyzed by FT-IR and ICP-AES to obtain the concentration of phosphorus in the PSG films formed under the above conditions from the thickness and density of the film. The above PSG film was formed under conditions that the concentration of phosphorus became 3.0 wt %. Another analysis method such as ICP-MS may be used for the analysis of the concentration of phosphorus. Thereafter, the substrate 1 having a PSG film only on a peripheral portion of the synthetic quartz substrate was manufactured by etching using a mask. The width of the PSG film shown in FIG. 1A was 3 mm.

Example 2

Manufacture of Synthetic Quartz Substrate Having a BPSG Film

A BPSG film was formed in place of the PSG film formed in Example 1. The substrate 1 having the BPSG film was manufactured in the same manner as in Example 1 except that $SiH_4$, $PH_3$, $B_2H_6$ and $O_2$ were used as raw material gases and the temperature of the substrate was changed to 450° C.

Example 3

Manufacture of Silicon Substrate Having a PSG Film: for Analysis by Dynamic SIMS A silicon substrate having a PSG film was manufactured basically in the same manner as in Example 1 except that a silicon substrate containing no impurities was used in place of the synthetic quartz substrate used in Example 1. The temperature of the substrate, the concentration of phosphorus and the thickness of the film were the same as in Example 1. The silicon substrate having a PSG film manufactured in this example was analyzed by SIMS.

Example 4

Dynamic SIMS of Silicon Substrate Having a PSG Film

To confirm that the concentration of phosphorus contained in the PSG film formed in Example 1 was constant in the depth direction, the PSG film formed in Example 3 was analyzed by dynamic SIMS to be indirectly evaluated.

Figure 5:
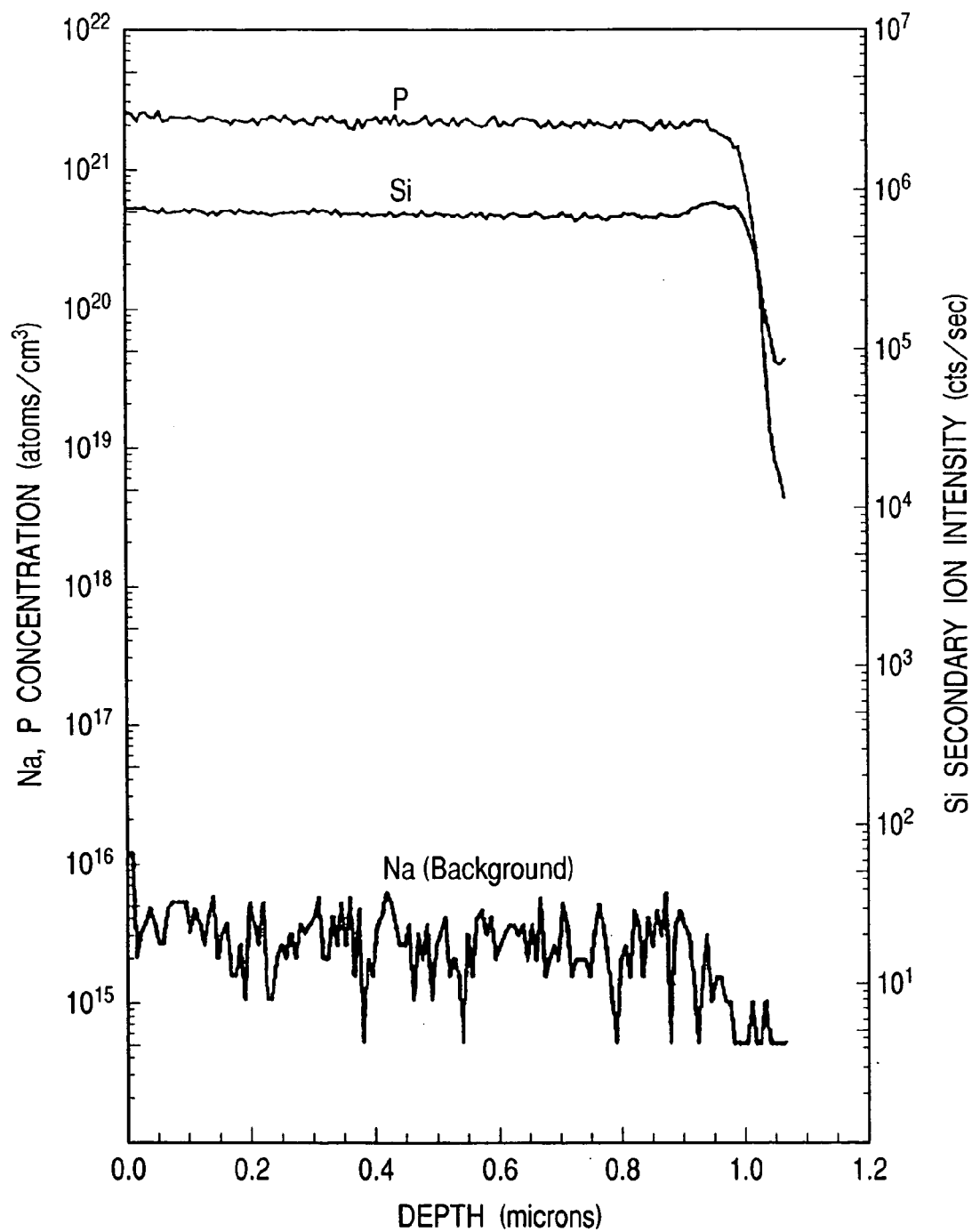
FIG. 5 is a graph showing an example of analytical results of dynamic SIMS of a PSG film on a silicon substrate.

The analysis results of dynamic SIMS obtained under standard conditions are shown in FIG. 5. As shown in FIG. 5, the concentration of phosphorus in the PSG film was almost constant. It was confirmed that right after CVD was started by the (B)PSG film forming apparatus, the concentration of phosphorus in the PSG film varied (about factor 2) but after a certain period of time, the concentration of phosphorus became substantially constant.

Example 5

Figure 2A:
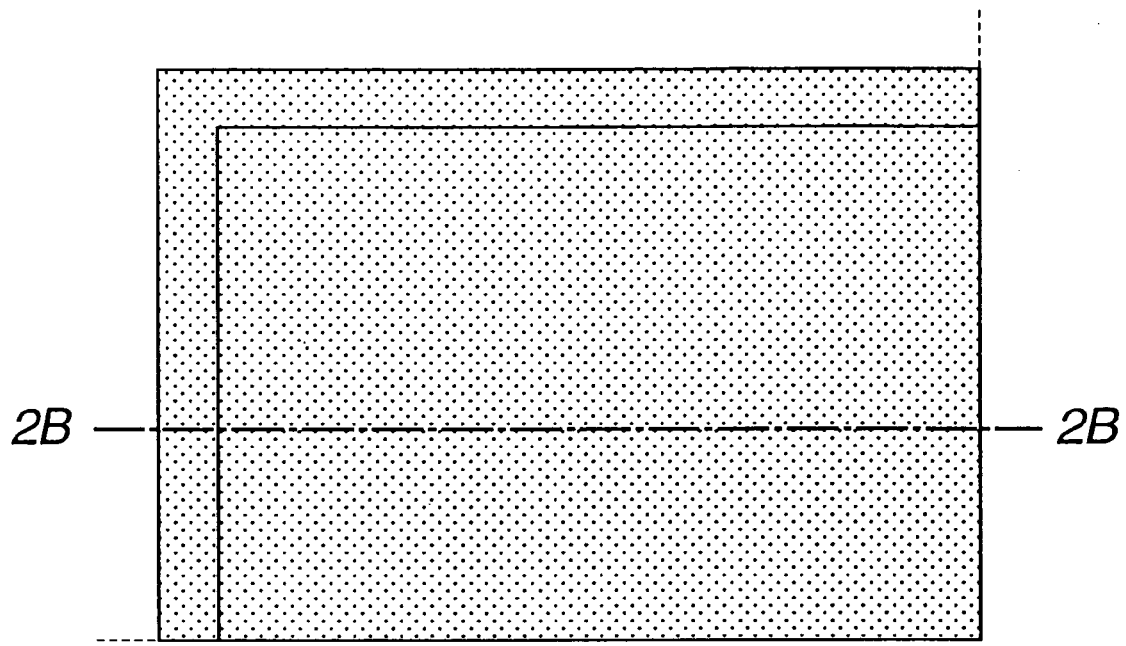
FIGS. 2A and 2B are schematic diagrams showing a process of producing a nucleic acid probe array using a synthetic quartz substrate having a PSG film.
Figure 2B:
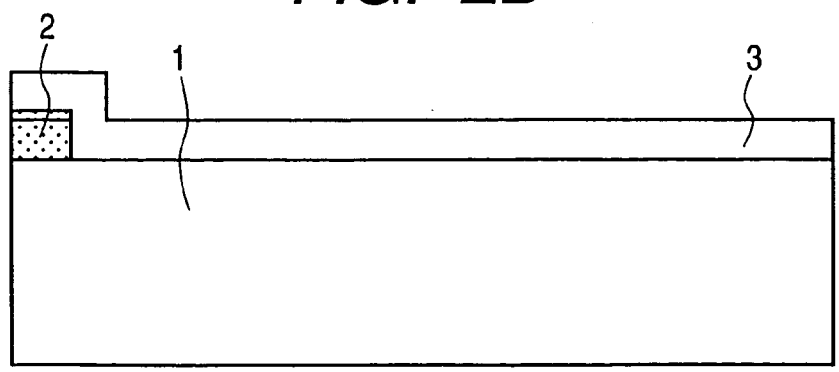
Figure 3A:
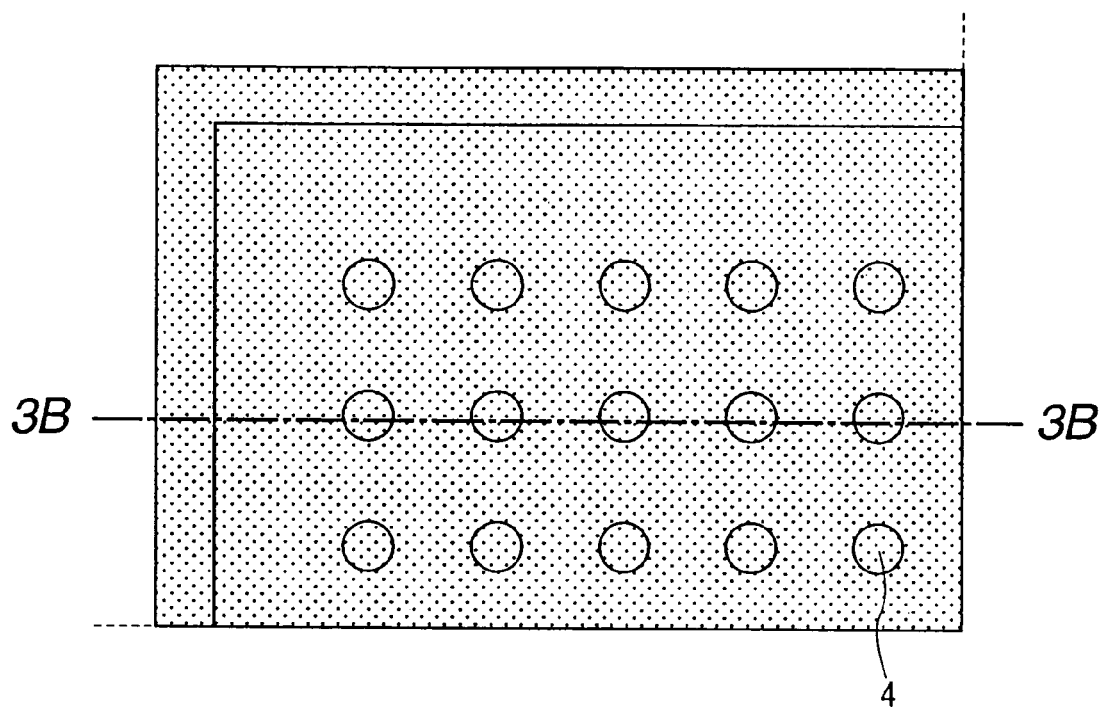
FIGS. 3A and 3B are schematic diagrams showing a process of producing a nucleic acid probe array using a synthetic quartz substrate having a PSG film.
Figure 3B:
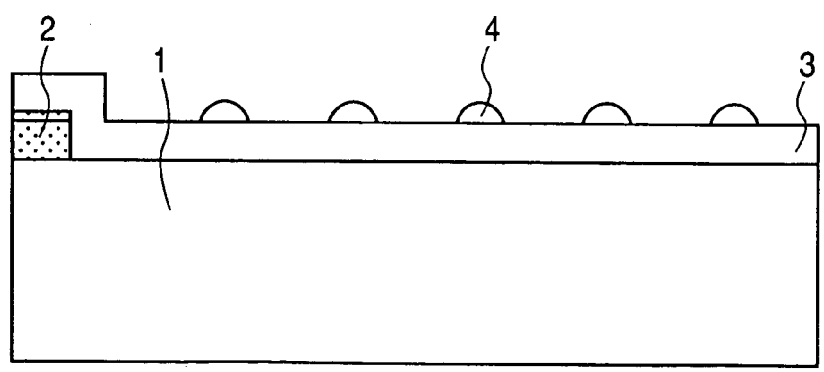

Manufacture of Synthetic Quartz Substrate Having a PSG Film and a Nucleic Acid Probe Array of dT40 Probes A nucleic acid probe array was produced using the synthetic quartz substrate having a PSG film manufactured in Example 1. This production process is schematically shown in FIGS. 2A and 2B and FIGS. 3A and 3B. FIG. 2A is a plan view, FIG. 2B is a sectional view taken along the line 2B—2B of FIG. 2A. FIG. 3A is a plan view and FIG. 3B is a sectional view taken along the line 3B—3B of FIG. 3A. Reference numeral 1 denotes the synthetic quartz substrate; 2, the PSG film; 3, the surface treated layer made from an organic material; and 4, the dot containing DNA. The method of producing a nucleic acid probe array will be described hereinbelow with reference to those figures. This method was based on the above method disclosed in JP H11-187900 A.

(1) Cleaning of Substrate

A synthetic quartz substrate 1 having the PSG film 2 manufactured in Example 1 was placed in a rack and immersed in an ultrasonic cleaner (Branson: GPIII) diluted with pure water to 10% overnight. Thereafter, the substrate was subjected to ultrasonic cleaning in the cleaner for 20 minutes and the cleaner is washed off with water. After it was rinsed in pure water, it was further subjected to the ultrasonic treatment in a container filled with pure water for 20 minutes. Then, the substrate was immersed in a 1N sodium hydroxide aqueous solution previously heated at 80° C. for 10 minutes. Subsequently, it was rinsed in water and pure water and the cleaned substrate was supplied to the next step.

(2) Surface Treatment

A 1 wt % aqueous solution of N-β-(aminoethyl)-γ-aminopropyl trimethoxysilane KBM 603, silane coupling agent having an amino group bonded thereto (Shinetsu Chemical Co., Ltd.) was stirred at room temperature for 2 hours to hydrolyze the methoxy group in the molecule of the above silane compound. The substrate obtained in (1) above was immersed in this solution at room temperature for 1 hour and rinsed in pure water, and a nitrogen gas was blown against both sides of the substrate to dry it. The substrate was baked in an oven heated at 120° C. for 1 hour to introduce the amino group onto the surface of the substrate in the end.

Thereafter, 2.7 mg of N-maleimidocaproyloxysuccinimide (Dojin Kagaku Kenkyusho Co., Ltd., hereinafter referred to as EMCS) was dissolved in a solution of dimethyl sulfoxide (DMSO)/ethanol (1:1) to a concentration of 0.3 mg/ml. A quartz substrate treated with a silane coupling agent was immersed in the EMCS solution at room temperature for 2 hours to react the amino group carried on the surface of the substrate by the silane coupling treatment with the succinimido group of the EMCS solution. In this stage, a maleimido group derived from the EMCS solution was existent on the surface of the substrate. The substrate taken out of the EMCS solution was cleaned with a DMSO/ethanol mixed solvent and ethanol sequentially, and a nitrogen gas was blown against the substrate to dry it. Thus, the synthetic quartz substrate 1 having the surface treated layer 3 made from the organic material and the PSG film 2 was manufactured (FIGS. 2A and 2B).

(3) Synthesis of Probe DNA

A DNA manufacturer (Bex Co., Ltd.) was asked to synthesize single-stranded nucleic acid having SEQ ID NO: 1 (40-mer of T). A thiol (SH) group was introduced into the 5' terminal of the single-stranded DNA having SEQ ID NO: 1 by using a thiol modifier (Glen Research Co., Ltd.) at the time of synthesis. Deprotection and the collection of DNA were carried out by specified methods and HPLC was used for purification. The manufacturer was asked to carry out a series of steps from synthesis to purification.

```
SEQ ID NO: 1
5' HS-(CH2)6-O-PO2-O-TTTTTTTTTT TTTTTTTTTT

TTTTTTTTTT TTTTTTTTTT 3'
```

(4) Discharge of DNA by Thermal Jet Printer and Bonding to Substrate

The above single-stranded DNA having SEQ ID NO: 1 was dissolved in a solution containing 7.5 wt % of glycerin, 7.5 wt % of urea, 7.5 wt % of thioglycol and 1 wt % of acetylene alcohol (trade name: Acetylenol EH; produced by Kawaken Fine Chemical Co., Ltd.) to a final concentration of 8 μM. The BC-50 printer head (manufactured by Canon Inc.) for the BJF-850 bubble jet printer (manufactured by Canon Inc.) using a bubble jet method as a kind of thermal jet method was modified to discharge several hundreds of μl of a solution. This head was mounted on a modified discharge-drawing machine so that the liquid could be discharged to the quartz substrate. The above DNA solution was injected into the modified tank of this head in an amount of several hundreds of μl and the EMCS-treated substrate was set in the discharge-drawing machine to spot the solution on the EMCS-treated substrate surface. The discharge amount of the solution at the time of spotting was 4 pl/droplet and the spotted area was 10 mm×10 mm on the center of the substrate at a pitch of 200 dpi, that is, 127 μm for the discharge. Under the above conditions, the diameter of dots spotted was about 50 µm.

After spotting, the substrate was left to stand in a humidifying chamber for 30 minutes to react a maleimido group on the surface of the glass substrate with a thiol group at the terminals of nucleic acid probes. Thereafter, the substrate was cleaned with pure water and kept in pure water. Thus, a nucleic acid probe array having the plural DNA-containing dots 4 on the synthetic quartz substrate 1 having the surface treated layer 3 made from an organic material and the PSG film 2 was manufactured (FIGS. 3A and 3B).

To analyze the DNA bonded substrate (DNA chip) by TOF-SIMS, the above DNA bonded substrate was dried by blowing a nitrogen gas and further dried in a vacuum desiccator right before analysis.

Comparative Example 1

Manufacture of Synthetic Quartz Substrate and Nucleic Acid Probe Array of dT40 Probes A nucleic acid probe array was produced by using a synthetic quartz substrate in place of the synthetic quartz substrate having the PSG film manufactured in Example 5. Other manufacturing steps were the same as in Example 5.

Example 6

TOF-SIMS

The dot formed portions and PSG film formed portion of the nucleic acid probe array of dT40 probes on the synthetic quartz substrate having the PSG film manufactured in Example 5 were analyzed by TOF-SIMS. The TOF-SIMS IV apparatus (manufactured by ION-TOF GmbH) was used for this measurement. The main measurement conditions are shown below.

Primary ion: 25 kV $Ga^+$, 0.6 pA (pulse current value), pulse frequency of random scan mode primary ion: 2.5 kHz (400 µs/shot)
Primary ion pulse width: 1 ns
Primary ion beam diameter: 5 µm
Primary ion scanning range (measurement range): 100 µm×100 µm
Dose of primary ion: about $1×10^{12}$ ions/cm$^2$
Detection mode of secondary ion: negative
Number of pixels of secondary ion image: 128×128
Integral number of times: 16

The TOF-SIMS measurement of the PSG film formed portion was carried out after the top of the above PSG film formed portion was etched by sputtering under the following conditions to expose the PSG film.

<Sputter Etching Conditions>
Etching ion: $O_2^+$ (using an ion gun in the TOF-SIMS apparatus)
Etching area: 500 µm×500 µm
For this etching, $CxHy^-$ ion derived from hydrocarbon on the surface and $PO_2^-$ ion derived from the PSG film were monitored at the same time, which was continued until the intensity of the $CxHy^-$ ion was reduced to a negligible level and the intensity of the $PO_2^-$ ion became constant.

Figure 4:
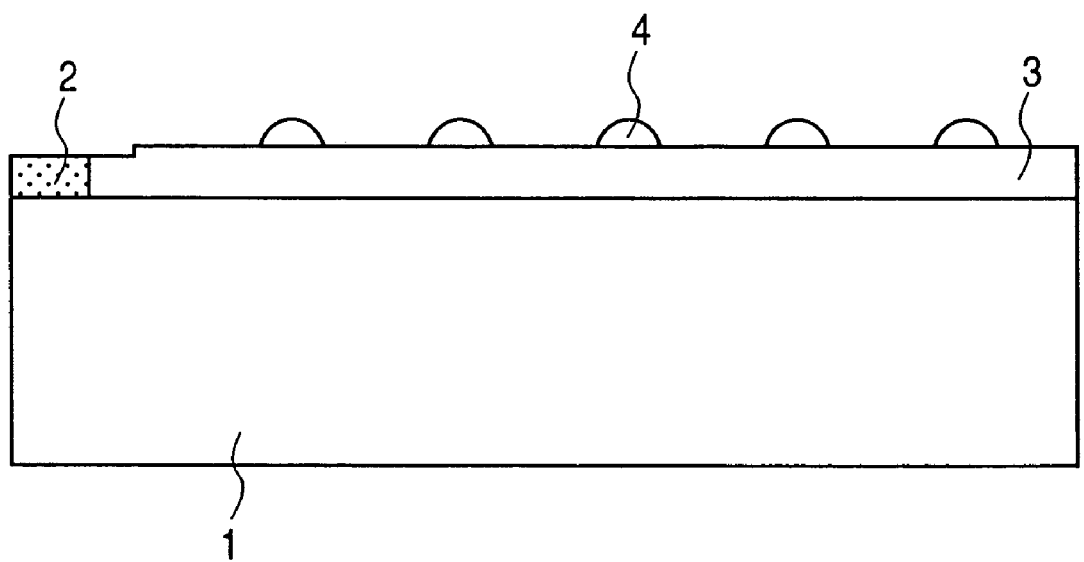
FIG. 4 is a sectional view of a nucleic acid probe array after sputter etching.

FIG. 4 is a sectional view of the above nucleic acid probe array after sputter etching. In FIG. 4, reference numeral 1 denotes the synthetic quartz substrate; 2, the PSG film; 3, the surface treated layer made from an organic material; and 4, the DNA-containing dot. Even when the PSG film is formed on the entire surface, this operation is needed.

When TOF-SIMS measurement was carried out in a portion where the PSG film 2 was exposed under the above conditions, the integral intensity of the above $PO_2^-$ ion was about 18,800 ions. When similar measurement was carried out five times by changing the measurement date, the integral intensity of the above $PO_2^-$ ion was 18,600 to 18,900 counts.

The intensity of the secondary ion from the fixed area of the above dot formed portions was standardized by the intensity of the major secondary ion (for example, $PO_2^-$) from the fixed area of the portion where the PSG film was exposed. The amount of a nucleic acid contained in each probe was thus evaluated.

On different dates, the above TOF-SIMS measurement was made on five nucleic acid probe arrays produced on different dates. As for the results of the five TOF-SIMS measurements, the intensity of the $PO_2^-$ ion from the dot portions was standardized by the intensity of the $PO_2^-$ ion from the above PSG film. As a result, variations in the latter ion intensity were within ±15%.

Comparative Example 2

TOF-SIMS

The nucleic acid probe array of dT40 probes on the synthetic quartz substrate manufactured in Comparative Example 1 was analyzed by TOF-SIMS under the same conditions as in Example 6. Since there was no PSG film on the synthetic quartz substrate in this example, this portion was not measured and only the intensity of the secondary ion from the fixed area of the dot formed portions was used because there was no secondary ion (intensity) which can standardize (become a standard).

On different dates, the above TOF-SIMS measurement was made on five nucleic acid probe arrays which were produced on different dates. The production dates of the nucleic acid probe arrays and the dates of the TOF-SIMS measurement were the same as in Example 6. In this case, variations in the intensity of the $PO_2^-$ ion from the dot portions (measurement values) were within ±30%.

Since the five nucleic acid probe arrays produced on different dates were analyzed in Example 6 and Comparative Example 2, the above variations in the intensity of the secondary ion occurred due to measurement variations and also due to variations in the nucleic acid probe arrays themselves. Although it is difficult to accurately find how much these variations contributed to the above variations, it is considered from the results of Example 6 and Comparative Example 2 that measurement variations could be reduced by standardization with the intensity of the major secondary ion (for example, $PO_2^-$ ion) derived at least from the PSG film.

Example 7

Figure 7:
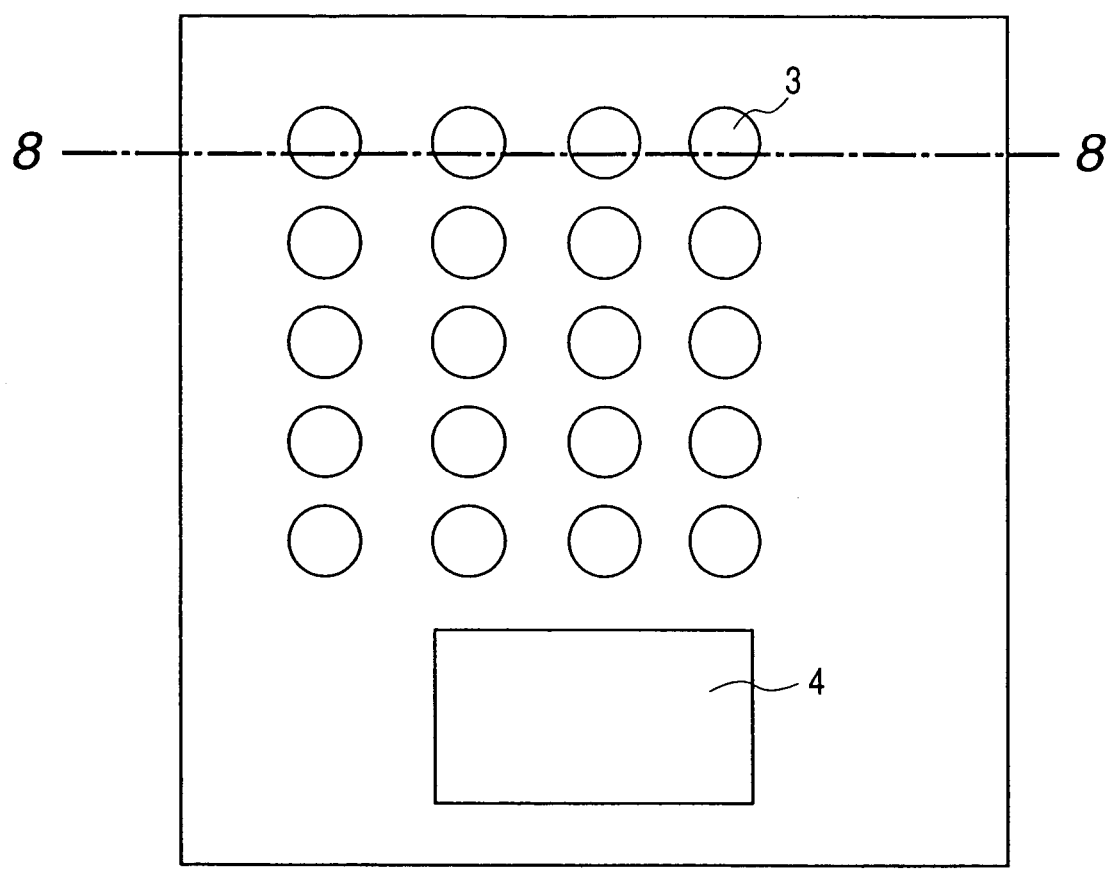
FIG. 7 is a schematic plan view of a nucleic acid chip substrate of the present invention.
Figure 8:
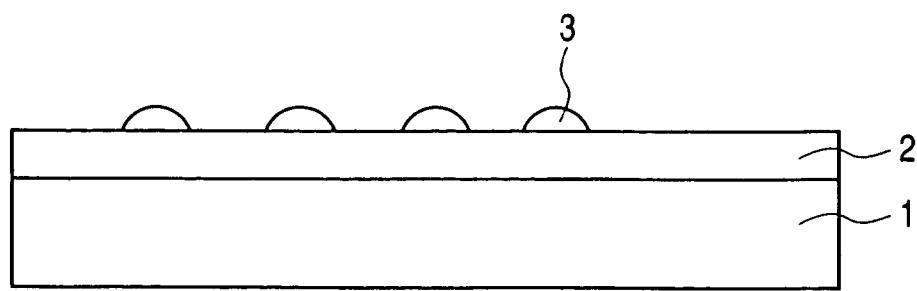
FIG. 8 is a schematic sectional view of the nucleic acid chip substrate of the present invention.
Figure 9:
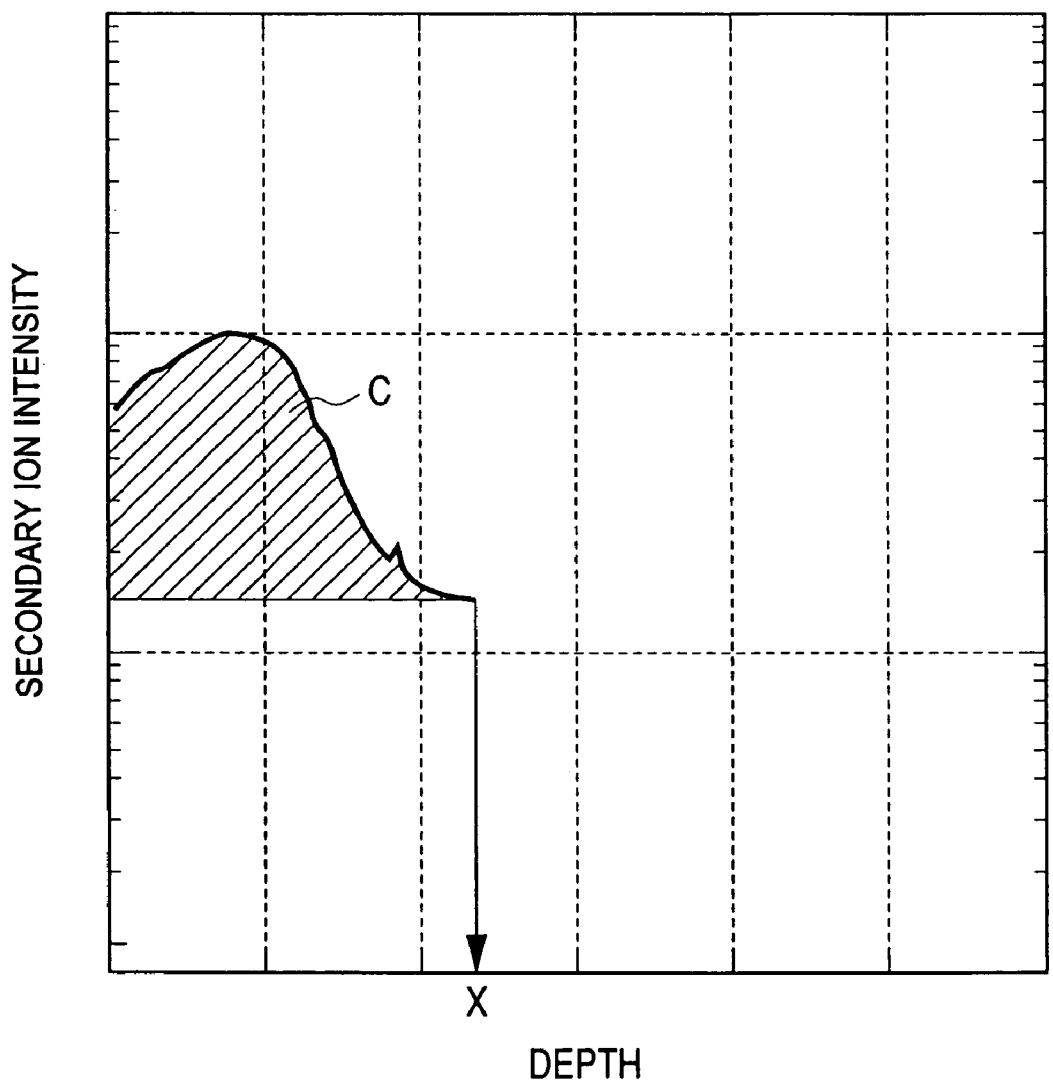
FIG. 9 is a graph showing a depth profile measured in a standard area.

Production of dT40 Nucleic Acid Chip Formed on Synthetic Quartz Substrate into Which Phosphorus Ions are Injected FIG. 7 is a schematic plan view of a nucleic acid dot array having the plural nucleic acids in the spot shape arranged on the substrate, and FIG. 8 is a schematic sectional view taken along the line 8—8 of FIG. 7. Reference numeral denotes the substrate; 2, the surface treated layer made from an organic material; 3, the nucleic acid dot; and 4, the standard area formed by implanting a known amount of phosphorus ions into the substrate. FIG. 7 shows a case where the standard area is formed on part of the substrate. The standard area may be formed on the entire surface of the substrate. FIG. 9 shows an example of a depth profile measured in the standard area 4.

The method of producing the dot array as shown in FIG. 7 and FIG. 8 will be described based on a known method (method disclosed in JP 11-187900 A).

(1) Cleaning of Substrate

A synthetic quartz substrate measuring 25.4 mm×25.4 mm×1 mm was placed in a rack and immersed in an ultrasonic cleaner (Branson: GPIII) diluted with pure water to 10% overnight. Thereafter, the substrate was subjected to ultrasonic cleaning in the cleaner for 20 minutes and the cleaner is washed off with water. After it was rinsed in pure water, it was further subjected to the ultrasonic treatment in a container filled with pure water for 20 minutes. Then, the substrate was immersed in a 1N sodium hydroxide aqueous solution previously heated at 80° C. for 10 minutes. Subsequently, it was rinsed in water and pure water.

(2) Ion implantation

Phosphorus (P) ions were implanted into the area 4 of the cleaned synthetic quartz substrate at implantation energy of 1 keV and a dose of $1\times10^{15}$ atoms/cm$^2$.

(3) Surface Treatment

FIG. 8 is a sectional view taken along the line 8—8 of FIG. 7.

A 1 wt % aqueous solution of N-β-(aminoethyl)-γ-aminopropyl trimethoxysilane KBM 603, silane coupling agent having an amino group bonded thereto (Shinetsu Chemical Co., Ltd.) was stirred at room temperature for 2 hours to hydrolyze the methoxy group in the molecule of the above silane compound. The substrate obtained in (2) above was immersed in this solution at room temperature for 1 hour and rinsed in pure water, and a nitrogen gas was blown against both sides of the substrate to dry it. The substrate was baked in an oven heated at 120° C. for 1 hour to introduce the amino group onto the surface of the substrate in the end.

Thereafter, 2.7 mg of N-maleimidocaproyloxysuccinimide (Dojin Kagaku Kenkyusho Co., Ltd., hereinafter referred to as EMCS) was dissolved in a solution of dimethyl sulfoxide (DMSO)/ethanol (1:1) to a concentration of 0.3 mg/ml. A quartz substrate 200 treated with a silane coupling agent was immersed in the EMCS solution at room temperature for 2 hours to react the amino group carried on the surface of the substrate by the silane coupling treatment with the succinimido group of the EMCS solution. In this stage, a maleimido group derived from the EMCS solution was existent on the surface of the substrate. The substrate taken out of the EMCS solution was cleaned with a DMSO/ethanol mixed solvent and ethanol sequentially, and a nitrogen gas was blown against the substrate to dry it. Thus, a surface treated layer 2 made from an organic material is formed on the synthetic quartz substrate 1.

(4) Synthesis of DNA Dots

A DNA manufacturer (Bex Co., Ltd.) was asked to synthesize single-stranded DNA having SEQ ID NO: 1 (40-mer of T (base)). A thiol (SH) group was introduced into the 5' terminal of the single-stranded DNA having SEQ ID NO: 1 by using a thiol modifier (Glen Research Co., Ltd.) at the time of synthesis. Deprotection and the collection of DNA were carried out by specified methods and HPLC was used for purification. The manufacturer was asked to carry out a series of steps from synthesis to purification.

```
SEQ ID NO: 1
5' HS-(CH2)6-O-PO2-O-TTTTTTTTTT TTTTTTTTTT

TTTTTTTTTT TTTTTTTTTT 3'
```

(5) Discharge of DNA by Thermal Jet Printer and Bonding to Substrate

The above single-stranded DNA having SEQ ID NO: 1 was dissolved in a solution containing 7.5 wt % of glycerin, 7.5 wt % of urea, 7.5 wt % of thioglycol and 1 wt % of acetylene alcohol (trade name: Acetylenol EH; produced by Kawaken Fine Chemical Co., Ltd.) to a final concentration of 8 µM. The BC-50 printer head (manufactured by Canon Inc.) for the BJF-850 bubble jet printer (manufactured by Canon Inc.) using a bubble jet method as a kind of thermal jet method was modified to discharge several hundreds of µl of a solution. This head was mounted on a modified discharge-drawing machine so that the liquid could be discharged to a quartz substrate. The above DNA solution was injected into the modified tank of this head in an amount of several hundreds of µl and the EMCS-treated substrate was set in the discharge-drawing machine to form the DNA dots on the substrate. The discharge amount of the solution at the time of forming the dots was 4 pl/droplet and the solution was discharged at a pitch of 200 dpi, that is, 127 µm. After forming the dots, the substrate was left to stand in a humidifying chamber for 30 minutes to react a maleimido group on the surface of the glass substrate with a thiol group at the terminals of DNA dots. Thereafter, the substrate was cleaned with pure water and kept in pure water. Thus, a nucleic acid chip having the plural DNA-containing dots 3 on the synthetic quartz substrate 1 having the surface treated layer 2 made from an organic material was produced (FIG. 7).

Example 8

Determination of Sensitivity Coefficient in Nucleic Acid Dot by SIMS

20 DNA chips were produced separately by forming dots (157 rows×236 columns) in a 20 mm×30 mm area on the substrate at intervals of 127 µm under the same conditions as the nucleic acid dots 3 of interest in the same manner as in Example 7 and then leaving them to stand in a humidifying chamber for 30 minutes to react a maleimido group on the surface of the glass substrate with a thiol group at the terminals of the DNA dots. After the DNA dots were dissolved through acid wash, the acid solution was concentrated to an amount of 1 ml or less under conditions that phosphorus was not scattered. Thereafter, ultra-pure water was added to this concentrated solution to adjust its volume to 1 ml. This solution was introduced into an ICP-MS apparatus to measure the weight of phosphorus. In consideration of the number of dots measured based on this value, an average formation density dav of the number of DNA molecules of the DNA dots produced in each concentration (number of phosphorus atoms per unit area) was determined. The number of substrates to be produced herein may be determined by the detection limit concentration of phosphorus of the ICP-MS apparatus (about 10 ppb) and the number of DNA molecules on each substrate and is not limited by the number of substrates shown herein.

Thereafter, each nucleic acid dot chip was introduced into the TOF-SIMS apparatus to apply the primary ion $Ga^+$ in a pulse form to dots on the nucleic acid chip at 10 kHz for a time t2 in order to measure the accumulative value of the intensity of the $P^-$ secondary ion from the plurality of dots and to obtain a sensitivity coefficient R1 of the nucleic acid dots from Iav determined as the average intensity of the secondary ion and the above average formation density dav previously obtained by chemical analysis (number of phosphorus atoms per unit area) based on the following equation (1).

$$R1 = dav/Iav \quad (1)$$

Example 9

TOF-SIMS Measurement of Nucleic Acid Chip

The determination of a nucleic acid in each dot of a nucleic acid chip was carried out as follows. First, the depth profile of phosphorus (P) in the standard area was measured using an ion gun for sputtering of TOF-SIMS and an ion gun for measurement alternately. As for the measurement, after a sputter ion was continuously applied for a time t1, a primary ion was applied in a pulse form for a time t2. Those operations were alternately performed until the final intensity of the $P^-$ secondary ion of interest became constant. The thus obtained depth profile is shown in FIG. 9. In FIG. 9, a sensitivity coefficient R2 under the above measurement conditions is obtained from a total count value C of the secondary ion $P^-$, a measurement depth X and a dose $\Phi$ of the ion implanted into the standard area based on the following equation (2).

$$R2 = \Phi/X \cdot C \quad (2)$$

From (1) and (2), $R1/R2 = dav/\{\phi \cdot (Iav/X \cdot C)\}$ where dav and $\phi$ are both known, so that when $dav/\{\phi \cdot (Iav/X \cdot C)\} = K$, $$R1 = R2 \cdot K \quad (3)$$

Thus, a parameter K between the sensitivity coefficient of the nucleic acid dot and the sensitivity coefficient of the standard area is determined. Then, an intensity I of the secondary ion is measured by applying the primary ion in a pulse form to the arbitrary nucleic acid dot 3 for a time t2. A formation density d of the nucleic acid dot 3 was determined as follows from the equations (1), (2) and (3).

$$d = I \cdot R1$$
$$= I \cdot R2 \cdot K$$

Example 10

Display of an Image of Formation Density Distribution

A plurality of nucleic acid dots of the same sample as in Example 9 were formed, a primary ion was scanned over the surface of the sample, the generated secondary ion was displayed for each scanning point, the intensity of $P^-$ obtained at each scanning point was classified into a plurality of levels, and a quasi color was set for each level to quantitatively compare the intensity distributions of $P^-$, that is, the formation density distributions as the surface density of a nucleic acid (number of nucleic acid molecules per dot).

Example 11

Production of dT40 Nucleic Acid Chip Formed on Glass Substrate Containing Phosphorus The nucleic acid chip substrate and the method of analyzing a biochip of the present invention will be described with reference to FIGS. 6, 10A to 10C, 11 and 12.

FIGS. 10A to 10C are diagrams showing the method of producing a nucleic acid chip substrate. FIG. 11 is a schematic plan view of a nucleic acid chip substrate having a probe array of a plurality of nucleic acids formed in a spot from on a substrate. FIG. 10C is a schematic sectional view taken along the line 10C—10C of FIG. 11. In those figures, reference numeral 1 denotes the substrate; 2, the surface treated layer made from an organic material; 3, the nucleic acid dot; and 4, the standard area used as a standard for determination (which may be set anywhere in a probe-free area of the substrate). FIG. 12 shows an example of the depth profile of the intensity of the secondary ion released from the substrate containing phosphorus (that is, the standard area). FIG. 6 shows an example of an analytical curve for obtaining the number of DNA molecules per dot by TOF-SIMS.

The method of producing a probe array as shown in FIGS. 10A to 10C and 11 will be described based on a known method (method disclosed in JP H11-187900 A).

(1) Preparation and Cleaning of the Substrate

First, after preparing a substrate containing phosphorus used for the nucleic acid chip substrate, cleaning of the substrate is carried out (FIG. 10A).

A glass substrate (25.4 mm×25.4 mm×1 mm) made from NeoCerum glass (composition (weight ratio): $SiO_2$: 67%, $Al_2O_3$: 23%, $LiO_2$: 4%, $TiO_2$: 2%, $ZrO_2$: 3%, $P_2O_5$: 1%) was prepared as the substrate containing phosphorus. Next, the substrate was placed in a rack and immersed in an ultrasonic cleaner (Branson: GPIII) diluted with pure water to 10% overnight. Thereafter, the substrate was subjected to ultrasonic cleaning in the cleaner for 20 minutes and the cleaner is washed off with water. After it was rinsed in pure water, it was further subjected to the ultrasonic treatment in a container filled with pure water for 20 minutes. Then, the substrate was immersed in a 1N sodium hydroxide aqueous solution previously heated at 80° C. for 10 minutes. Subsequently, it was rinsed in water and pure water.

(2) Surface Treatment

The surface treatment of the substrate is then carried out to form the surface treated layer 2 formed from an organic material on the substrate 1 (FIG. 10B).

A 1 wt % aqueous solution of N-β-(aminoethyl)-γ-aminopropyl trimethoxysilane KBM 603, silane coupling agent having an amino group bonded thereto (Shinetsu Chemical Co., Ltd.) was stirred at room temperature for 2 hours to hydrolyze the methoxy group in the molecule of the above silane compound. The substrate obtained in (2) above was immersed in this solution at room temperature for 1 hour and rinsed in pure water, and a nitrogen gas was blown against both sides of the substrate to dry it. The substrate was baked in an oven heated at 120° C. for 1 hour to introduce the amino group onto the surface of the substrate in the end.

Thereafter, 2.7 mg of N-maleimidocaproyloxysuccinimide (Dojin Kagaku Kenkyusho Co., Ltd., hereinafter referred to as EMCS) was dissolved in a solution of dimethyl sulfoxide (DMSO)/ethanol (1:1) to a concentration of 0.3 mg/ml. The substrate treated with a silane coupling agent was immersed in the EMCS solution at room temperature for 2 hours to react the amino group carried on the surface of the substrate by the silane coupling treatment with the succinimido group of the EMCS solution. In this stage, a maleimido group derived from the EMCS solution was existent on the surface of the substrate. The substrate taken out of the EMCS solution was washed with a DMSO/ethanol mixed solvent and ethanol sequentially, and a nitrogen gas was blown against the substrate to dry it.

Thus, the surface treated layer 2 made from an organic material is manufactured on the glass substrate 1.

(3) Preparation of Nucleic Acid

A DNA manufacturer (Bex Co., Ltd.) was asked to synthesize single-stranded DNA having SEQ ID NO: 1 as the nucleic acid (40-mer of T (base)). A thiol (SH) group was introduced into the 5' terminal of the single-stranded DNA having SEQ ID NO: 1 by using a thiol modifier (Glen Research Co., Ltd.) at the time of synthesis. Deprotection and the collection of DNA were carried out by specified methods and HPLC was used for purification. The manufacturer was asked to carry out a series of steps from synthesis to purification.

```
SEQ ID NO: 1
```
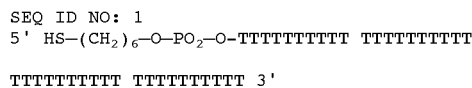

```
   TTTTTTTTTT TTTTTTTTTT 3'
```

(4) Formation of Probes on Substrate

A nucleic acid chip having the plural probes 3 containing a nucleic acid formed on the substrate 1 having the surface treated layer 2 made from an organic material was produced (FIG. 10C). FIG. 10C is a schematic sectional view taken along the line 10C—10C of FIG. 11.

The above single-stranded DNA having SEQ ID NO: 1 was dissolved in a solution containing 7.5 wt % of glycerin, 7.5 wt % of urea, 7.5 wt % of thiodiglycol and 1 wt % of acetylene alcohol (trade name: Acetylenol EH; manufactured by Kawaken Fine Chemical Co., Ltd.) to a concentration of 8 μM. The BC-50 printer head (manufactured by Canon Inc.) for the BJF-850 bubble jet printer (manufactured by Canon Inc.) using a bubble jet method as a kind of thermal jet method was modified to discharge several hundreds of μl of a solution and mounted on a modified discharge-drawing machine so that the liquid could be discharged to the above quartz substrate. The above DNA solution was injected into the modified tank of this head in an amount of several hundreds of μl and the EMCS-treated substrate was set in the discharge-drawing machine to form DNA probes on the substrate. The discharge amount of the solution for forming probes was 4 pl/droplet and the pitch was set to 200 dpi, that is, 127 μm for the discharge. After the formation of probes, the substrate was left to stand in a humidifying chamber for 30 minutes to react a maleimido group on the surface of the glass substrate with a thiol group at the terminals of DNA probes. Then, the substrate was cleaned with pure water and kept in pure water. A nucleic acid chip substrate having the plural probes 3 containing DNA as a nucleic acid formed on the glass substrate 1 having the surface treated layer 2 made from an organic material was thus produced.

Example 12

TOF-SIMS Measurement

The quantitative analysis of a nucleic acid in each probe of the nucleic acid chip was carried out using the nucleic acid chip substrate produced in Example 11.

Quantitative evaluation is made possible by correcting the intensity of the secondary ion released from each dot of the nucleic acid chip and the intensity of the secondary ion released from the substrate containing phosphorus (standard area) with their secondary ionization efficiencies (sensitivities) or the like. FIG. 12 shows an example of the depth profile of the intensity of the secondary ion released from the substrate containing phosphorus.

The standard nucleic acid chip whose probe nucleic acid density had been obtained by chemical analysis or the like was produced on the substrate containing phosphorus in order to obtain a relational expression (analytical curve) between the above two intensities in advance. A specific example of the above relational expression (analytical curve) is shown in FIG. 6. After obtaining this relational expression (analytical curve), the number of DNA molecules per dot, that is, the probe nucleic acid density was evaluated based on the intensity of the secondary ion such as $P^-$, $PO^-$, $PO_2^-$ or $PO_3^-$ released from the substrate containing phosphorus.

This enables the quantitative analysis of a nucleic acid in each probe to be made.

Example 13

Display of an Image of Formation Density Distribution

An area including a plurality of DNA probes of the same sample as in Example 12 was set, a primary ion was scanned over the surface of the sample, and the generated secondary ion was displayed for each scanning point. The same measurement was carried out, the count value of $PO_3^-$ obtained at each scanning point was classified into different levels, and a quasi color was set for each level to quantitatively compare the intensity distributions, that is, the formation density distributions.

Example 14

Production of dT40 Nucleic Acid Chip Formed on Glass Substrate Containing Phosphorus A nucleic acid chip substrate was produced in the same manner as in Example 11 except that a glass substrate (25.4 mm×25.4 mm×1 mm) made from the JSSCR-1 glass (composition (weight ratio): $SiO_2$: 72.2%, $Al_2O_3$: 1.75%, $Fe_2O_3$: 0.08%, $TiO_2$: 0.03%, CaO: 6.72%, MgO: 4.01%, $Na_2O$: 13.8%, $K_2O$: 0.84%, $SO_3$: 0.20%, $P_2O_5$: 0.02%, $As_2O_3$: 0.07%) was prepared as the substrate containing phosphorus (P).

Example 15

TOF-SIMS Measurement

The analysis of a nucleic acid in each probe of a nucleic acid chip was carried out using the nucleic acid chip substrate produced in Example 14 in the same manner as in Example 12. Quantitative evaluation could be made.

Example 16

Display of an Image of Formation Density Distribution

An image of the formation density distribution of a nucleic acid in each probe of a nucleic acid chip was displayed using the nucleic acid chip substrate produced in Example 14 in the same manner as in Example 13. Quantitative comparison of the formation density distribution could be performed.

Comparative Example 3

Production of dT40 Nucleic Acid Chip Formed on Glass Substrate Containing no Phosphorus A nucleic acid chip substrate was produced in the same manner as in Example 11 except that a substrate (25.4 mm×25.4 mm×1 mm) made from quartz (composition: $SiO_2$: 100%) was prepared as the substrate containing no phosphorus.

Comparative Example 4

TOF-SIMS Measurement

The quantitative analysis of a nucleic acid in each probe of a nucleic acid chip was carried out using the nucleic acid chip substrate produced in Comparative Example 3 in the same manner as in Example 12. Since there was no standard area containing phosphorus, highly accurate quantitative evaluation could not be made.

Comparative Example 5

Display of an Image of Formation Density Distribution

An image of the formation density distribution of a nucleic acid in each probe of a nucleic acid chip was displayed using the nucleic acid chip substrate produced in Comparative Example 3 in the same manner as in Example 12. Since there was no standard area containing phosphorus, highly accurate image display could not be performed.

According to the present invention, the intensity of $PO_2^-$ released from dots containing a nucleic acid such as DNA or a secondary ion derived from a base is standardized by the intensity of a secondary ion such as $PO_2^-$ released from an area containing phosphorus in a fixed concentration, whereby it is possible to quantitatively evaluate the amount of a nucleic acid probe in each dot, the amount of a probe base and the total amount of nucleic acids after hybridization. By obtaining the sensitivity coefficients of both, the absolute values of the amount of a nucleic acid and the amount of a base can be theoretically obtained.

---

---

What is claimed is:

1. A method for analyzing a probe carrier having a probe immobilized area in which a nucleic acid probe is immobilized and a probe-free phosphorus-containing area that contains phosphorus in a predetermined concentration on a carrier, comprising:

detecting an amount of the phosphorus contained in the nucleic acid probe in the probe immobilized area as a first signal intensity;

detecting an amount of the phosphorus in the probe-free phosphorus-containing area as a second signal intensity; and determining the nucleic acid probe amount in the probe immobilized area by standardizing the first signal intensity by using the predetermined concentration of the phosphorus in the probe-free phosphorus-containing area and the second signal intensity.

2. A method for analyzing a probe carrier according to claim 1, wherein the plurality of probes immobilized areas is each arranged independently on the carrier in a matrix form.

3. A method for analyzing a probe carrier according to claim 1, wherein the probe-free phosphorus-containing area is formed by implanting the phosphorus into at least a portion of the carrier.

4. A method for analyzing a probe carrier according to claim 3, wherein the probe-free phosphorus-containing area is formed as a film formed on at least a portion of a surface of the carrier.

5. A method for analyzing a probe carrier according to claim 4, wherein a concentration of the phosphorus in the film is fixed in a depth direction.

6. A method for analyzing a probe carrier according to claim 1, wherein the probe-free phosphorus-containing area is formed by containing the phosphorus in an entire portion forming the surface having the probe immobilized area of the carrier.

7. A method for analyzing a probe carrier according to claim 6, wherein the carrier constitutes the surface having the probe immobilized areas and the entire carrier is composed of a substrate which uniformly contains the phosphorus.

8. A method for analyzing a probe carrier according to claim 7, wherein the carrier is composed of a glass substrate.

9. A method for analyzing a probe carrier according to claim 6, wherein the content (weight ratio) of the phosphorus in the probe-free phosphorus-containing area is $0.1 \times 10^{-4}$ wt % or more and 10 wt % or less.

10. A method for analyzing a probe carrier according to claim 4, wherein the film is made from phosphorus silicate glass (PSG) or boron phosphorus silicate glass (BPSG).

11. A method for analyzing a probe carrier according to claim 1, wherein the nucleic acid probe has a nucleic acid that is at least one selected from the group consisting of DNA, RNA, peptide nucleic acid (PNA), complementary DNA (cDNA), and complementary RNA (cRNA).

12. A method for analyzing a probe carrier according to claim 5, wherein the phosphorus concentration of another film which is formed under the same condition as the film which contains the phosphorus and has the fixed phosphorus concentration in the depth direction is analyzed by at least one analysis method selected from the group consisting of:
1) secondary ion mass spectrometry: SIMS;
2) time-of-flight secondary ion mass spectrometry (TOF-SIMS);
3) X-ray photoelectron spectroscopy: XPS;
4) Auger electron spectroscopy: AES;
5) inductively coupled plasma atomic emission spectroscopy: ICP-AES;
6) inductively coupled plasma mass spectrometry: ICP-MS; and
7) Fourier transforms infrared spectroscopy: FT-JR, and determined based on an analytical result thereof.

13. A method for analyzing a probe carrier according to claim 1, wherein the first signal intensity and the second signal intensity each comprise a secondary ion intensity detected by time-of-flight secondary ion mass spectrometry (TOF-SIMS).

14. A method for analyzing a probe carrier according to claim 13, wherein the secondary ion is one selected from the group consisting of $P^-$, $PO^-$, $PO_2^-$ and $PO_3^-$.

15. A method for analyzing a probe carrier according to claim 4, wherein the signal intensity detected from the film is a signal intensity obtained after the area is etched by sputtering in a fixed amount.

16. A method for analyzing a probe carrier according to claim 1, wherein an image of an arrangement of the nucleic acid probe immobilized areas can be quantitatively displayed.

* * * * *

UNITED STATES PATENT AND TRADEMARK OFFICE
CERTIFICATE OF CORRECTION

| | |
|---|---|
| PATENT NO. | : 7,208,276 B2 |
| APPLICATION NO. | : 10/728707 |
| DATED | : April 24, 2007 |
| INVENTOR(S) | : Hiromitsu Takase et al. |

It is certified that error appears in the above-identified patent and that said Letters Patent is hereby corrected as shown below:

Title page, item (56), the reference corresponding to U.S. Patent No. "5,601,980 A" should have the class identified as --435--.

Title page, item (56), the reference corresponding to U.S. Patent No. "5,821,060 A" should have the class identified as --435--.

Title page, item (56), the reference corresponding to Lazzeri, et al. should read --20009-- instead of "200009" as the source of the citation.

Column 26, claim 12, line 7, "FT-JR" should read --FT-IR--.

Signed and Sealed this

Seventh Day of August, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 40
<212> TYPE: DNA
<213> ORGANISM: artificial
<220> FEATURE:
<223> OTHER INFORMATION: probe

<400> SEQUENCE: 1 ttttttttttt tttttttttt tttttttttt tttttttttt                40